US010859571B2

(12) United States Patent
Heller et al.

(10) Patent No.: US 10,859,571 B2
(45) Date of Patent: Dec. 8, 2020

(54) METHOD AND A SYSTEM FOR QUANTITATIVE OR QUALITATIVE DETERMINATION OF A TARGET COMPONENT

(71) Applicant: Zoetis Denmark ApS, Farum (DK)

(72) Inventors: Martin Bak Heller, Søborg (DK); Bent Overby, Glostrup (DK); Niels Kristian Bau-Madsen, Hellerup (DK)

(73) Assignee: ZOETIS DENMARK ApS, Farum (DK)

( * ) Notice: Subject to any disclaimer, the term of this patent is extended or adjusted under 35 U.S.C. 154(b) by 0 days.

(21) Appl. No.: 14/409,703

(22) PCT Filed: Jun. 21, 2013

(86) PCT No.: PCT/DK2013/050208
§ 371 (c)(1),
(2) Date: Dec. 19, 2014

(87) PCT Pub. No.: WO2013/189502
PCT Pub. Date: Dec. 27, 2013

(65) Prior Publication Data
US 2015/0247845 A1 Sep. 3, 2015

(30) Foreign Application Priority Data

Jun. 22, 2012 (DK) .................................. 2012 70353

(51) Int. Cl.
*G01N 33/543* (2006.01)
*B01L 3/00* (2006.01)
(Continued)

(52) U.S. Cl.
CPC .... *G01N 33/54333* (2013.01); *B01L 3/50273* (2013.01); *B01L 3/502715* (2013.01); *B01L 3/502761* (2013.01); *B82Y 15/00* (2013.01); *G01N 21/6428* (2013.01); *G01N 21/6489* (2013.01); *G01N 33/04* (2013.01); *G01N 33/12* (2013.01); *G01N 33/5005* (2013.01); *G01N 33/53* (2013.01); *G01N 33/54326* (2013.01); *G01N 33/54386* (2013.01); *G01N 33/569* (2013.01); *G01N 33/582* (2013.01); *G01N 33/587* (2013.01); *G01N 33/588* (2013.01); *B01L 2200/0668* (2013.01); *B01L 2300/0654* (2013.01); *B01L 2300/0663* (2013.01); *B01L 2300/087* (2013.01); *B01L 2300/0816* (2013.01); *B01L 2300/0877* (2013.01); *B01L 2300/123* (2013.01); *B01L 2300/18* (2013.01);
(Continued)

(58) Field of Classification Search
CPC ......... G01N 33/54333; G01N 21/6428; G01N 21/6489; G01N 33/04; G01N 33/12; G01N 33/5005; G01N 33/53; G01N 33/54326; G01N 33/54386; G01N 33/569; G01N 33/582; G01N 33/587; G01N 33/588; G01N 2021/6439; G01N 2021/6441; G01N 2021/6448; G01N 2033/0095; B01L 3/502715; B01L 3/50273; B01L 3/502761; B01L 2200/0668; B01L 2300/0654; B01L 2300/0663; B01L 2300/0816; B01L 2300/087; B01L 2300/0877; B01L 2300/123; B01L 2300/18; B01L 2400/043; B01L 2400/0481; B01L 2400/049; B82Y 15/00
See application file for complete search history.

(56) References Cited

U.S. PATENT DOCUMENTS 4,331,337 A   5/1982   Cross et al.
4,347,312 A   8/1982   Brown et al.
(Continued)

FOREIGN PATENT DOCUMENTS

EP   1 827 693 B1   3/2010
EP   2 287 611 A1   2/2011
(Continued)

OTHER PUBLICATIONS

Chan et al., "Magnetic Scanometric DNA Microarray Detection of Methyl Tertiary Butyl Ether Degrading Bacteria for Environmental Monitoring," Biosensors and Bioelectronics, (Jan. 15, 2011), vol. 26, No. 5, pp. 2060-2066.
(Continued)

*Primary Examiner* — Andrea S Grossman
(74) *Attorney, Agent, or Firm* — Buchanan Ingersoll & Rooney P.C.

(57) ABSTRACT

A method and a system for quantitative or qualitative determination of a target component in a liquid sample includes i) providing a plurality of magnetic particles including one or more capture sites for the target component on their respective surfaces; ii) providing a plurality of fluorophores configured to bind to the capture sites of the magnetic particles; iii) bringing the liquid sample into contact with the fluorophores and the magnetic particles in a flow channel of a micro fluidic device including a transparent window; and iv) at least temporally immobilizing the magnetic particles adjacent to the transparent window using a magnet, emitting exciting electromagnetic beam towards the immobilized magnetic particles, reading signals emitted from fluorophores captured by the immobilized magnetic particles and performing a quantitative or qualitative determination of the target component based on the read signal.

20 Claims, 9 Drawing Sheets

(51) Int. Cl.
*G01N 33/58* (2006.01)
*G01N 33/50* (2006.01)
*G01N 33/53* (2006.01)
*G01N 33/569* (2006.01)
*B82Y 15/00* (2011.01)
*G01N 21/64* (2006.01)
*G01N 33/04* (2006.01)
*G01N 33/12* (2006.01)
*G01N 33/00* (2006.01)

(52) U.S. Cl.
CPC ... *B01L 2400/043* (2013.01); *B01L 2400/049* (2013.01); *B01L 2400/0481* (2013.01); *G01N 2021/6439* (2013.01); *G01N 2021/6441* (2013.01); *G01N 2021/6484* (2013.01); *G01N 2033/0095* (2013.01)

(56) References Cited

U.S. PATENT DOCUMENTS

| | | | |
|---|---|---|---|
| 4,731,337 A | 3/1988 | Luotola et al. | |
| 6,562,581 B2* | 5/2003 | Law | G01N 33/723 435/14 |
| 7,498,177 B2 | 3/2009 | De La Fuente et al. | |
| 2002/0006670 A1* | 1/2002 | Wu | G01N 33/5005 436/514 |
| 2003/0011382 A1* | 1/2003 | Chow | B01L 9/527 324/601 |
| 2004/0043507 A1* | 3/2004 | Song | B01L 3/502761 436/514 |
| 2004/0043512 A1* | 3/2004 | Song | G01N 33/54326 436/526 |
| 2004/0115817 A1* | 6/2004 | Liu | C09K 11/025 435/472 |
| 2006/0003336 A1* | 1/2006 | Song | G01N 33/558 435/6.16 |
| 2008/0032420 A1* | 2/2008 | Lambert | G01N 33/54373 436/514 |
| 2008/0160634 A1* | 7/2008 | Su | B01L 3/502761 436/501 |
| 2009/0155838 A1* | 6/2009 | Hale | A61J 1/2093 435/29 |
| 2009/0270269 A1 | 10/2009 | Kumar et al. | |
| 2010/0248258 A1 | 9/2010 | Lee et al. | |
| 2010/0254858 A1 | 10/2010 | Paulraj et al. | |
| 2010/0311186 A1* | 12/2010 | Gregory | B03C 1/01 436/501 |
| 2011/0025315 A1 | 2/2011 | Ohtsuka | |
| 2012/0275929 A1* | 11/2012 | Salsman | F04B 43/04 417/53 |

FOREIGN PATENT DOCUMENTS

| | | |
|---|---|---|
| JP | 2002-525394 A | 8/2002 |
| JP | 2008238168 A | 10/2008 |
| JP | 2009019971 A | 1/2009 |
| JP | 2011033454 A | 2/2011 |
| JP | 2013536952 A | 9/2013 |
| WO | 00/17655 A1 | 3/2000 |
| WO | 2007/092713 A2 | 8/2007 |
| WO | 2008/109675 A1 | 9/2008 |
| WO | 2010/042242 A1 | 4/2010 |
| WO | 2010041230 A2 | 4/2010 |
| WO | 2010/141105 A2 | 12/2010 |
| WO | 2011/026030 A1 | 3/2011 |
| WO | 2012/016107 A1 | 2/2012 |
| WO | 2012/032294 A1 | 3/2012 |

OTHER PUBLICATIONS

Chan et al., "Luminescent Quantum Dots for Multiplexed Biological Detection and Imaging," Current Opinion in Biotechnology, (Feb. 1, 2002), vol. 13, Issue 1, pp. 40-46.

Henares et al., "Current Development in Microfluidic Immunosensing Chip," Analytica Chimica Acta, (Mar. 17, 2008), vol. 611, Issue 1, pp. 17-30.

Yang et al., "Micro Flow Cytometry Utilizing a Magnetic Bead-Based Immunoassay for Rapid Virus Detection," Biosensors and Bioelectronics, (2008), vol. 24, pp. 855-862.

Safarik et al., "Magnetic Techniques for the Isolation and Purification of Proteins and Peptides," BioMagnetic Research and Technology, (Nov. 26, 2004), vol. 2, pp. 1-17.

International Search Report dated Sep. 12, 2013, by the Nordic Patent Institute in corresponding International Application No. PCT/DK2013/050208. (5 pages).

Feng et al., "Functionalized Europium Oxide Nanoparticles used as a Fluorescent Label in an Immunoassay for Atrazine," Analytical Chemistry, (2003), vol. 75, No. 19, pp. 5282-5286.

Kuang et al., "Recent Developments in Analytical Applications of Quantum Dots," Trends in Analytical Chemistry, (Nov. 2011), vol. 30, No. 10, pp. 1620-1636.

The extended European Search Report dated Feb. 11, 2016, by the European Patent Office in corresponding European Patent Application No. 13807718.5-1554. (10 pages).

Office Action (Notification of Reasons for Refusal) dated May 9, 2017, by the Japanese Patent Office in corresponding Japanese Patent Application No. 2015-517612, and an English Translation of the Office Action. (6 pages).

* cited by examiner

METHOD AND A SYSTEM FOR QUANTITATIVE OR QUALITATIVE DETERMINATION OF A TARGET COMPONENT

TECHNICAL FIELD

The present invention relates to a method and a system for quantitative or qualitative determination of a target component in a liquid sample, in particular a biologic target component or optionally several target components in the same liquid sample.

BACKGROUND ART

A plurality of methods and devices for quantitative or qualitative determination of a target component in a liquid sample are known from the prior art. Many of these prior art methods comprise complicated or time consuming steps, such as washing steps. For many years new and improved methods have constantly been developed, and in particular methods using optical labeling and read out systems.

The use of magnetic particles with capture probes has also been explored in several methods.

A fluorimetric immunological assay with magnetic particles is described in U.S. Pat. No. 4,731,337. In this document it was suggested to perform a test using plastic pearls comprising a magnetic substance and carrying antigen for an antibody to be studied in a transparent test tube. The pearls are put into the test tube together with a sample containing the antibody to be studied as well as an antibody marked with a fluorescent molecule. Upon completion of the reaction, the quantity of the marked antibody adhering to the antigen on the solid phase is measured in a fluorometer, in which both the excitation radiation is passed into the sample and the fluorescent radiation is collected to the detector through the bottom of the measurement vessel. Moreover, the fluorometer is provided with means for generating a magnetic field, and by its means the pearls are pulled against the bottom of the measurement vessel for the time of the measurement. Moreover, before the measurement, a coloring agent is added to the sample to absorb intensively at the wavelength of the excitation radiation or of the emission radiation in order to reduce interference by the excess tracer remaining in the liquid phase or by the background radiation with the measurement.

The above method has, however, never been used in practice.

WO 2010/042242 discloses for example a use of magnetic particles in combination with a fluidic device. The fluidic device disclosed herein has a main channel, wherein a first inlet fluidly connects to an upstream end of the main channel and the method comprises introduction of magnetic beads into the channel. The magnetic beads are configured to bind to a target. A magnet is applied to magnetically move the magnetic beads through various sections of the fluidic device to allow the magnetic beads to capture a target, to a washing step and other steps required for obtaining a quantification of the target captured on the magnetic beads.

WO 2008/109675 discloses a device and method for the capture of magnetic beads in a rotary magnetic bead trap. The device allows capture, washing, elution and ejection of beads in an automated system. Analyte is eluted in a small volume in a capillary-scale fluid system compatible with LC-MS/MS analysis.

US 2010/0248258 discloses a microfluidic chip and method for rapid detection of different target proteins. The microfluidic chip utilizes antibody-conjugated magnetic beads to bind to the target proteins to form a magnetic complex, and then use the signal labeled-antibodies that can recognize the magnetic complex. The method comprises purifying the magnetic complex by the micro-magnetic field on biochip, and introducing the purified magnetic complex into the fluorescent detection area on the chip to detect the amount of the target protein in the purified complex immediately.

U.S. Pat. No. 4,347,312 discloses a method for detecting the presence of antibiotics in milk which comprises the steps of: (a) contacting a solid matrix having attached thereto a purified immobilized antibody with a volume of milk and an enzyme-labeled antibiotic, the antibody being specific to the antibiotic; (b) separating the matrix from the milk and rinsing the matrix with water to remove excess milk and enzyme-labeled antibiotic; (c) contacting the rinsed matrix with a substrate, the substrate in the presence of the enzyme-labeled antibiotic exhibiting a color change the amount of which is quantitatively related to the amount of enzyme-labeled antibiotic; and (d) measuring the amount of antibiotic present in the milk by comparing the color change in the substrate with a standard. Also provided is a method for producing purified antibodies for use in the foregoing detection method by: (a) covalently conjugating an antibiotic having a lactam-ring in the molecule to a protein capable of binding thereto through the lactam-ring; (b) injecting into a host animal capable of raising antibodies specific to the antibiotic the conjugate obtained in step (a) so as to raise the specific antibodies; (c) covalently conjugating the same antibiotic in step (a) to a second protein capable of binding thereto through the lactam-ring and different than the protein used in step (a) to form a second conjugate; (d) covalently binding the second conjugate to a solid matrix to form an affinity matrix for purifying the antibodies; (e) isolating and purifying the specific antibodies raised in step (b) by contacting the host animal serum with the affinity matrix; and (f) recovering the specific antibodies in a pure form.

DISCLOSURE OF INVENTION

An object of the present invention is to provide a new method for quantitative or qualitative determination of a target component in a liquid sample, which method is simple and fast and where it is possible to perform determinations of two or more target components simultaneously.

An object of the present invention is further to provide a system for performing quantitative or qualitative determination of a target component in a liquid sample where the cost for each determination is relatively low.

In an embodiment of the invention it is further an object to provide a method which does not require time consuming washing steps and preferably where it is possible to perform a determination relatively fast e.g. in a few minutes.

These objects have been achieved by the present invention and embodiments hereof as defined in the claims and described below.

The invention has shown to provide a completely new approach for quantitative or qualitative determination of a target component in a liquid.

Further it has been found that very good and accurate results can be obtained in a fast and simple way.

The method of the invention for quantitative or qualitative determination of a target component in a liquid sample, comprises providing a plurality of magnetic particles comprising one or more capture sites for the target component on their respective surfaces;

providing a plurality of fluorophores configured to bind to the capture sites of the magnetic particles;

bringing the liquid sample, the fluorophores and the magnetic particles into a flow channel of a micro fluidic device comprising a transparent window; and at least temporally immobilizing the magnetic particles adjacent to the transparent window using a magnet, emitting exciting electromagnetic beam(s) towards the immobilized magnetic particles, reading signals emitted from fluorophores captured by the immobilized magnetic particles and performing a quantitative or qualitative determination of the target component based on the read signal.

The method of the invention is highly suitable for qualitative determination of one or more target components and it has been found that the method can provide highly accurate results. However, the method of the invention has also shown to be very suitable for qualitative determinations e.g. for screening purposes. Examples of this will be described further below.

The "method" is also referred to by the term "test" and a liquid which is subjected to the method of the invention is tested/subjected to a test.

The term "at least temporally immobilizing the magnetic particles adjacent to the transparent window" should be taken to mean that the magnetic particles should be immobilized for a sufficient time to excite possible fluorophores captured on the magnetic particles and read signals emitted from such fluorophores. This will be further described below.

The liquid sample, the fluorophores and the magnetic particles are fed into the flow channel of the micro fluidic device, such that they are in contact with each other. In an embodiment two or all of the liquid sample, the fluorophores and the magnetic particles are brought into contact before being fed into the liquid channel. In an embodiment the liquid sample, the fluorophores and the magnetic particles are brought into contact within the liquid channel The transparent window is for example in the form of a transparent wall section of the flow channel.

By performing the test using a micro fluid device, the method becomes very fast and only a small amount of sample is required.

Heretofore when performing tests using magnetic particle for capturing marked components, it has been an ordinary requirement that some kind of washing was required or at least a masking of false positive was required in order to obtain a useful determination. By using micro fluidic device for performing the test it has surprisingly been found that washing is not required and not even desired. In fact it is preferred that after the magnetic particles are immobilized, no further liquid should be added and in a preferred embodiment the liquid in the flow channel is at standstill, meaning that there is no flow and no turbulence within the flow channel. Further it is desired that no light absorbing elements are added beyond what is inherently in the sample. In an embodiment the sample comprises no added light absorbing elements beyond the fluorophores and the magnetic particles and what is inherent in the liquid sample. In an embodiment the sample comprises no elements absorbing light emitted by the fluorophores beyond the fluorophores and the magnetic particles.

The method has shown to give surprisingly reliable results even while determining two or more target components simultaneously.

Preferred micro fluidic devices will be described further below.

The term "liquid sample" means any liquid containing sample including liquid sample comprising solid parts, such ad dispersions and suspensions. The sample comprises liquid at the time of performing the method.

In principle any liquid sample can be applied, including but not limited to liquid samples comprising particles, such as dispersed particles. The liquid sample is in one embodiment crushed food or tissue optionally blended with water or it may be an extract thereof. Thus, the method of the invention can for example be applied for performing quantitative and/or qualitative tests on tissue, vegetables, meat and etc.

In an embodiment the liquid sample comprises human or animal faeces e.g. in an aqueous suspension.

In an embodiment the liquid sample comprises waste water or water from a nature source e.g. a lake or a river.

The liquid sample should preferably have a sufficiently low viscosity for being mixed with the fluorophores and the magnetic particles preferably such as to allow possible present target components to bind to the magnetic particles. If the viscosity is too high, the sample may be diluted with liquid, such as water prior to testing. In an embodiment of the invention the liquid sample is tested in several dilutions and e.g. in undiluted condition for improving the accuracy of the determination.

In an embodiment the liquid sample comprises a biological fluid or a fraction of a biological fluid. Examples of such biological fluids include human or animal or vegetable fluids, such as blood, saliva, urine, milk, cytosol (intracellular fluid), interstitial fluid (tissue fluid) and/or one or more fractions and/or mixtures thereof.

The term "a target component" means one or more molecules of a specific type of components. The term "two or more or several target components" means two or more or several different types of target components"

A type of components comprises components which can be captured by a specific capture site on the magnetic particles. The components included in a type of components can be identical components or it can be components with a certain similarity including that they can be captured by a specific capture site on the magnetic particles.

In the following the term "target component" is for simplification mainly used in singular, but it should also include the plural version of the term "target components" unless otherwise specified.

The term "target component" and "target analytes" are used interchangeably.

The target component can in principle be any kind of target component which can be determined in a binding assay. The skilled person can in a simple manner use knowledge from other types of binding assays to select suitable target components and corresponding capture sites to be provided on the magnetic particles.

In the following it should be understood that the method for quantitative and/or qualitative determination can be performed on one or more target components simultaneously, and unless otherwise specified the singular term 'target component' should be interpreted to also include the plural term 'target components'.

In an embodiment the target component is a biomolecule, such as a single organic molecule or a structure of organic molecules e.g. an organic organism. Since there are high needs in the industry e.g. the health care industry, the food industry, the method of the invention is highly suitable for use in quantitative and/or qualitative determinations of biomolecules, in particular because the method of the invention is both very fast and highly reliable.

In an embodiment of the invention, the target component may for example be a mutant variant of a molecule or an organic organism, such as a microorganism.

In an embodiment, the target component is or comprises a microorganism such as at least one of bacterial, viral or fungal pathogens, e.g. *E-coli E. coli, Citrobacter* spp, *Aeromonas* spp., *Pasteurella* spp., non-serogroup DI *Salmonella, Camphylobacter Staphylococcus* spp and combinations thereof.

In an embodiment, the target component is or comprises a cell, such as a blood cell, a stem cell or a tumor cell.

In an embodiment, the target component is or comprises proteins, nucleotides, carbohydrates, or lipids, in particular an enzyme, an antigen or an antibody.

In an embodiment the target component is or comprises a "hapten". A hapten is a small molecule that can elicit an immune response only when attached to a large carrier such as a protein; the carrier may be one that does not elicit an immune response by itself. The hapten may for example be a steroid, a hormone, an antibiotic or an inorganic constituent.

The skilled person will realize that the target component can be any kind of component for which a capture cite can be provided.

Target components and corresponding capture sites are well known in the art. Also it is well known to immobilize such capture sites on a surface such as magnetic particles.

Examples of capture sites and magnetic particles comprising such capture sites for microorganism target component can for example be found in WO2012016107.

The capture sites are selected in relation to at least one target component, such that the capture sites bind to at least one target component.

In an embodiment of the method of the invention, the magnetic particles are coated magnetic particles comprising a coating comprising the captures sites, wherein the capture sites are selected to be capture sites for the target component, the coating for example comprises the capture sites in the form of antigen, antibody, avidine, biotin or Goat anti-Mouse IgG.

In an embodiment the capture sites are specific for the target component.

If there are two or more target components there may be several groups of capture sites or there may be one type of capture sites that are capture sites for all target components.

In an embodiment where there are two or more target components, the capture sites are specific for the two or more target components e.g. for a group of similar but not identical target components.

In an embodiment of the invention, the capture sites are specific for a group of components comprising one or more target components.

In an embodiment the capture sites are for example binding sites for protein, the protein content can thereby be determined. In an embodiment the capture sites are binding sites for a pre-selected type or group of proteins.

In an embodiment the binding sites are binding sites for haptens such as small organic molecules e.g. steroid hormones, antibiotics or even other hapten molecules of other origin.

The magnetic particles may in principle have any size which is suitable for handling in the micro fluidic device.

The use of magnetic particle technology in quantitative and qualitative biological tests, particularly antibody-coated magnetic beads and immunomagnetic beads have become widely used and magnetic particles for such test are commercially available in many forms.

Methods for constructing immunomagnetic particles are generally known in the art (e.g. Safarik, I. and Safarikova, M. "Magnetic techniques for the isolation and purification of proteins and peptides.: BioMagn. Res. Technol. 2 (2004)).

The magnetic particles are preferably of micro or nano size. Preferably the magnetic particles have an average size of up to about 50 μm, more preferably up to about 25 μm, such as from about 1 to about 20 μm.

The magnetic particles may be spherical or non-spherical. Some examples of magnetic particles include Cortex Megacell™-Streptavidin magnetic particles, Cortex Megabeads™-Streptavidin CM3454 (8.8 μm particle size and coated with magnetizable polystyrene/iron oxide particles), Cortex Megabeads™-Streptavidin CTM-C M019 (15.6 μm particle size and coated with polystyrene copolymer/iron oxide particles), Dynabeads™ M-280-Streptavidin (3-4 μm particle size), and Genpoint BugTrap™ magnetic beads.

Other examples of suitable magnetic particles are the magnetic particles available from Spherotech, Inc. US. Ademtech, France including for example smaller size magnetic beads size of 200-500 nm, i.e. functionalized with streptavidin, protein A or/and G plus a number of different antibodies. Product 03152 MasterBeads StreptAvidin (Mean Diameter: ~500 nm); product 03231 Bio-Adembeads StreptAvidin plus (Mean Diameter: ~300 nm); product 03221 Bio-Adembeads streptavidin plus product (Mean Diameter: ~200 nm); 02650 Active-Masterbeads (Mean Diameter: ~500 nm) for direct protein conjugation.

Banglabs Inc, US, BM549 BioMag® Goat anti-Mouse IgG (Mean Diameter: ~1.5 μm); BM551/10272 BioMag® Streptavidin (Mean Diameter: ~1.5 μm); BM553/9750 BioMag® Protein G (Mean Diameter: ~1.5 μm); PMS3N/10098 ProMag™ 3 Series●Streptavidin (Mean Diameter: ~3.28 μm); CM01N COMPEL™ Magnetic Streptavidin modified (Mean Diameter: ~8 μm).

Fluorophores are well known in the art and are widely used within the technology of quantitative and qualitative assays.

A fluorophore (also called a fluorochrome or a florescent chromophore) is a molecule which can be excited by absorbing light energy and re-emits energy at a specific wavelength. The wavelength, amount, and time before emission of the emitted energy depend on both the fluorophore and its chemical environment as the molecule in its excited state may interact with surrounding molecules.

The excitation energy may be a very narrow or a broader band of energy, or it may be all energies beyond a cut-off level. The emission energy and wavelength is usually more specific than the excitation energy, and it is usually of a longer wavelength or lower energy. Excitation energies range from ultraviolet through the visible spectrum, and emission energies may continue from visible light into the near infrared region.

Generally it is desired to select fluorophores with a relatively specific emission wavelength and energy for a simpler qualitative or quantitative determination of the target component. In particular it is desired that the emission wavelength is relatively specific, i.e. it should preferably have a wavelength band which in the method of determination is sufficiently narrow to be distinguished from other emissions.

The term "relative specific wavelength" means that the wavelength can be distinguished from other emitting wavelengths in the test.

In particular in situations where there are several different fluorophores and optionally several target components it is preferred that the fluorophores have relatively specific emission wavelengths such that emission from the respective fluorophores can be distinguished from each other.

The fluorophores can be any type of fluorophores which can be configured to bind to the capture sites of the magnetic particles. Fluorophores are well known to the skilled person and are commercially available.

Examples of quantum dots are described in U.S. Pat. No. 7,498,177 and the quantum dots available from Life Technologies Europe BV. include more than 150 different product configurations with emission wavelength spanning in a broad wavelength range for examples quantum dots with the respective emission wavelengths: 525, 545, 565, 585, 605, 625, 655 and IR 705 and 800 nm. In an embodiment StreptAvidin, Biotin, antibodies and a number of different functionalities have been conjugated in the Invitrogen/life Technologies portfolio of Quantum dot products.

Examples of quantum dots also include quantum dots available from Ocean NanoTech, Springdale, Ark. 72764, including more than 40 different product configurations with emission wavelength spanning in nm and a functionalized outer core of PEG or other biological compatible coating, for example with the respective emission wavelengths: 530, 550, 580, 590, 600, 610, 620 and 630 nm. The quantum dots from Ocean NanoTech include quantum dots with different functional groups e.g. amine, COOH, phenylboronic acid (PBA), as well as quantum dots with amphiphilic polymer and PEG coating. Other examples of quantum dots available from Ocean NanoTech are quantum dots with a sole core e.g. provided in toluene and with only an octadecylamine coat or with amphiphilic polymer and PEG coating.

In an embodiment the fluorophores are quantum dots or aromatic probes and/or conjugated probes, such as fluorescein, derivatives of benzene, metal-chalcogenide fluorophores or combinations thereof.

The fluorophores are preferably configured to bind to the capture sites of the magnetic particles by being coupled to a component which can bind to the capture sites of the magnetic particles.

In an embodiment the component is identical to the target component. In most situations it is most simple to configure the fluorophores to bind to the capture sites by coupling the fluorophores to a component which is identical to a target component.

In an embodiment the component is homolog to the target component. If for example the target component is a pathogen, an expensive or rare component or in certain other situations it may be very beneficial to configure the fluorophores to bind to the capture sites by coupling the fluorophores to a target component homolog.

The term "a component homolog to a target component" means herein that the component should have a homology to the target component such that at least some of the homolog components will bind to the capture sites of the magnetic particles when applied in a competitive assay of equal molar amount of the target component and the homolog component.

In a preferred embodiment of the invention the fluorophores are quantum dots that emit one or more discrete frequencies of light when stimulated by a light source. In this embodiment several different quantum dots can be excited with the same wavelength or at least with a light beam having a relatively small band width.

Preferably each quantum dot comprises a core of an excitable material, such as a semiconductor nanoparticle or a rare earth doped oxide colloidal nanoparticle.

In an embodiment, the quantum dots comprise each a core with a size of up to about 25 nm, such as from 2-10 nm. The quantum dots preferably are coated with an organic coating, such as a polymer coating. Preferably the coating is coupled to a component which can bind to the capture sites of the magnetic particles e.g. such as described above.

In an embodiment of the invention, each of the quantum dots comprises a core of a binary semiconductor alloy, such as cadmium-selenide, cadmium-sulphide, indium-arsenide or indium-phosphide, covered with a transparent shell optionally comprising or consisting of Zinc sulphide.

The liquid sample, one or more of the fluorophores and one or more of the magnetic particles may in principle be brought into contact with each other in any order as well as outside the micro fluidic device or in the flow channel of the micro fluidic device.

In an embodiment the liquid sample is brought into contact with one or more of said fluorophores and one or more of said magnetic particles outside the flow channel of the micro fluidic device and thereafter the liquid sample is fed to the flow channel of the micro fluidic device.

In an embodiment of the invention, the liquid sample is brought into contact with one or more of the fluorophores and one or more of the magnetic particles outside the micro fluidic device in the form of a micro fluidic device and thereafter the liquid sample is fed to a flow channel of the micro fluidic device.

In an embodiment the magnetic particles and the liquid sample are brought into contact with each other e.g. in a syringe or a secondary test tube prior to application of the liquid sample in the flow channel of the micro fluidic device, where after the liquid sample with the magnetic particles is fed into the flow channel of the micro fluidic device and the liquid sample is mixed with the fluorophores in the flow channel of the micro fluidic device. In this situation the target component—if present in a sufficient amount—will be captured on essentially all capture sites of the magnetic particles and there will not be any or almost none detectable emission from fluorophores. If on the other hand a large emission signal is detected, it can be concluded that the target component is not present in the liquid sample.

In an embodiment the fluorophores and the liquid sample are brought into contact with each other e.g. in a syringe or a test tube prior to application of the liquid sample into the flow channel of the micro fluidic device and the liquid sample is mixed with the magnetic particles in the flow channel of the micro fluidic device. In this situation the target component—if present—will compete with the fluorophores about the capture sites of the magnetic particles and the detected emission signal will provide information about the amount of the target component.

In an embodiment the fluorophores, the magnetic particles and the liquid sample are brought into contact with each other e.g. in a syringe or a test tube prior to application of the liquid sample into the flow channel of the micro fluidic device and the liquid sample is fed to the flow channel of the micro fluidic device for determination. In this situation target component—if present—will compete with the fluorophores about the capture sites of the magnetic particles and the reactions (competition) will initiate outside the micro fluidic device, and no further mixing or reaction time (incubation) in the flow channel of the micro fluidic device may be required.

In a preferred embodiment the liquid sample is brought into contact with one or more of the fluorophores and the magnetic particles in the flow channel of the micro fluidic device.

In an embodiment the fluorophores and the magnetic particles are arranged in the flow channel of the micro fluidic device, and the method comprises feeding the liquid sample into the flow channel, the fluorophores and the magnetic particles are preferably arranged in the flow channel at a distance from each other.

In an embodiment the fluorophores and the magnetic particles are arranged in the flow channel of the micro fluidic device and the method of the invention comprises feeding the liquid sample into the flow channel, the fluorophores and the magnetic particles are preferably arranged in the flow channel at a distance from each other.

The fluorophores and the magnetic particles should preferably be applied in the flow channel of the micro fluidic device such that the capture sites of the magnetic particles do not capture any substantial amount of fluorophores prior to intermixing with the liquid sample. The fluorophores and the magnetic particles may be applied by any method e.g. by drying out in sections of the flow channel. In an embodiment the fluorophores and/or the magnetic particles are applied by producing the micro fluidic device in a substrate with a groove for the flow channel and a lid and the fluorophores and/or the magnetic particles are applied prior to adding the lid to the micro fluidic device.

In an embodiment the fluorophores and the magnetic particles are temporally immobilized in the flow channel of the micro fluidic device of the micro fluidic device such that they cannot bind to each other prior to the feeding of the liquid sample to the flow channel.

It is well known to temporally immobilize components in micro fluidic devices and any of such well known methods can be applied in the method of the invention.

The magnetic particles may for example be temporally immobilized by magnetic forces.

In an embodiment the fluorophores and/or the magnetic particles are temporally immobilized by being dried in the flow channel.

When the liquid sample comes in contact with the temporally immobilized fluorophores and/or the temporally immobilized magnetic particles the fluorophores and/or the magnetic particles are resuspended. The term "resuspended" is herein used to mean that the fluorophores/magnetic particles are dissolved or suspended in the liquid.

In an embodiment the magnetic particles are permanently immobilized by magnetic forces and the liquid sample is forced to flow into contact with the magnetic particles. Since only a small amount of possible target components will come into reach of the capture sites of the magnetic particles in this embodiment, it is generally desired that the magnetic particles are free to intermix with the liquid sample, i.e. the magnetic particles should preferably not be permanently immobilized.

The liquid sample may be fed into the flow channel by any method and means, e.g. by pipetting, by using a syringe, by dripping into the inlet or by being sucked into the flow channel of the micro fluidic device in the form of a fluidic device.

In an embodiment of the invention the liquid sample is fed into the flow channel of the micro fluidic device by being sucked into the flow channel, the suction is provided by an actuator. The actuator is advantageously arranged to move a flexible wall section of the flow channel or of a sink section in fluid connection with the flow channel.

The actuator may preferably be arranged to move the flexible wall section of the flow channel or the sink section to provide a suction to suck the liquid sample into the flow channel. The flow channel preferably comprises a first feeding end and a second actuator end comprising the flexible wall section. In an embodiment the flow channel in combination with a sink section in fluid connection comprises a first feeding end and a second actuator end comprising the flexible wall section, where the second actuator end is a part of or all of the sink section.

In order to obtain an accurate quantitative determination, the method preferably comprises allowing the capture sites of the magnetic particles to capture possible target component in the liquid sample and/or fluorophores. The reaction time is usually very short e.g. from seconds to a few minutes, such as about 10 minutes or less. The reaction time is preferably about 1 minute or less. In a preferred embodiment, the method comprises stirring and/or pulsating the liquid sample in the flow channel. Such pulsation can for example be provided using an actuator. After a certain pre-selected reaction time the magnetic particles are at least temporally immobilized adjacent to the transparent window using a magnet.

In an embodiment where the magnet is a permanent magnet, the magnetic particles will immediately be attracted to the magnet after the sample is introduced into the flow channel. If the magnetic force is of a suitable strength e.g. as described below, the magnetic particles will be pulled towards the transparent window at a suitable speed such that the reaction with possible target components and fluorophores will have taken place before immobilization for at least a part of the capture sites of the magnetic particles and preferably for most or substantially all of the capture sites. If the test is a quantitative test, the reaction time can usually be shorter than when the test is a qualitative test.

The transparent window is advantageously a window of the flow channel of the micro fluidic device.

The term "transparent" means herein that the window is transparent for the excitation and emission wavelengths of the fluorophores. Accordingly the windows need not be transparent for visual inspection, however, generally it is desired that the window or preferably the whole flow channel is transparent for visual inspection.

Generally it is known to produce micro fluidic devices and examples of general production methods and materials can be found in e.g. US 2010/0254858 and EP 1 827 693.

In an embodiment a wall section or the whole wall of the flow channel is preferably transparent.

Generally it is desired that the magnet has a magnetic field sufficiently strong to at least temporally immobilize the magnetic particles adjacent to the transparent window.

The magnet may in principle be any type of magnet with a suitable strength. In an embodiment the magnet is selected to generate a magnetic field adjacent to the transparent window for immobilizing the magnetic particles, which magnet field is from about 0.05 to about 1 tesla, such as from about 0.1 to about 0.5 tesla, such as from about 0.15 to about 0.3 tesla.

The magnetic field need not be homogeneous. In an embodiment the magnet provides a magnetic field of from about 0.2 to about 0.3 tesla in a distance of about 1 mm and a magnetic field of from about 0.01 to about 0.2 tesla in a distance of about 2.5 mm. In an embodiment the magnet provides a magnetic field in a distance of 2.5 mm which is about from ⅓ to ½ the strength of the magnetic field in a distance of about 1 mm.

If the magnet is undesirably strong it may provide a too fast immobilization of the magnetic particles i.e. the capture sites of the magnetic particles may not have suitable time to bind target component or fluorophores prior to immobilization of the magnetic particles. This is of course only relevant if the magnet is a permanent magnet. If the magnet is undesirably weak, it may not be able to immobilize a sufficient amount of magnetic particles. By a few tests the skilled person can find a suitable magnet strength adapted to a specific method of the invention.

The magnet may preferably be a permanent magnet, for the reason of simplification and low cost. However, in an embodiment an electromagnet, such as an adjustable electromagnet may be suitable e.g. if magnetic forces are applied in the mixing of the liquid sample with the fluorophores and/or the magnetic particles.

The magnet may be movable or stationary depending on the setup for performing the method of the invention. For a simple structure it is desired that the magnet is stationary arranged to immobilize the magnetic particles for excitation and read out adjacent to the transparent window.

In a preferred embodiment the at least temporally immobilized magnetic particles are subjected to the electromagnetic beam such that at least a part of possible fluorophores captured by the capture sites of the magnetic particles are excited, where after the emitted signal from the possibly captured fluorophores are read and a quantitative or qualitative determination of the target component based on the read signal is performed.

It has been found that where the fluid in the flow channel after the magnetic particles are immobilized using the magnet is at standstill, the at least temporally immobilized magnetic particles remain immobilized at least for a time such as up to several minutes after releasing the magnetic particles from influence of the magnetic force of the magnet. Thereby the magnet can be removed from the transparent window and making room for an emitter to excite the fluorophores and a reader to read out any signal from the fluorophores. Thereby the emitter and/or reader can be positioned where the magnet previously was positioned which has shown to provide extremely reliable results. In an embodiment the emitter is arranged to emit the electromagnetic beam via one or more emitting optical fibers comprising output ends arranged immediately adjacent to the transparent window (e.g. where the magnet was arranged when immobilizing the magnetic particles) In an embodiment the receiver is arranged to receive the signal from the fluorophores via one or more receiver optical fibers comprising input ends arranged immediately adjacent to the transparent window (e.g. where the magnet was arranged when immobilizing the magnetic particles).

The output ends of the emitting optical fibers and the input ends of the receiver optical fibers are advantageously arranged in a pattern. In an embodiment the output ends of the emitting optical fibers are arranged in a circle surrounding the input ends of the receiver optical fibers. In an embodiment the input ends of the receiver optical fibers are arranged in a circle surrounding the output ends of the emitting optical fibers. In an embodiment one or more lenses are arranged to collect the signal and direct it to the input ends of the receiver optical fibers.

Methods of excitation of fluorophores are well known in the art. The exciting wavelength is preferably adjusted to the excitation peak of the fluorophores. In an embodiment the excitation light is a relative band emission and preferably relatively low energy, such that the excitation light does not result in an undesired heating of the liquid sample or the elements therein.

In an embodiment the micro fluidic device is kept at a controlled temperature to optimize the bonding and ensuring that an undesired temperature does not interfere with the binding assay.

In an embodiment of the invention, the plurality of fluorophores is substantially identical.

If only one target component is to be determined, it is often desired that the fluorophores applied are substantially identical with respect to excitation and emitting, however, it should be understood that one target component can in principle be detected using different types of fluorophores in the same test.

In a preferred embodiment of the invention, the plurality of fluorophores comprises two or more groups of fluorophores, wherein the two or more groups of fluorophores differ from each other with respect to types, sizes, coatings, shape and/or amounts.

If two or more groups of fluorophores are present they may in principle be selected independently of each other, but preferably such that they emit at different wavelengths. In this situation it is particularly preferred to apply quantum dots as fluorophores, because quantum dots at different sizes emit at different wavelengths while they are excited at substantially the same wavelength.

The amount of fluorophores is preferably selected to provide an estimated competition for possible target components on the liquid sample. The amount of fluorophores can be determined by a few tests. A possible outset for selecting the amount of fluorophores is to select an amount of about 0.02 to about 100 times the amount which corresponds to the maximal estimated amount of target component in the liquid sample, such as an amount of about 1 to about 50 times or an amount of about 10 to about 50 times the amount which corresponds to the maximal estimated amount of target component in the liquid sample. For improved accuracy of the result, it is often desired to repeat the determination of a target component in a liquid sample using different amounts of fluorophores.

The amount of fluorephore may for example vary from about 0.02 to about 50 nM (nano mol), preferably from about 0.1 to about 10 nM.

The magnetic particles may be equal or different from each other. In an embodiment the magnetic particles are substantially identical with respect to capture sites and optionally with respect to number of capture sites and/or size.

In an embodiment the plurality of magnetic particles comprises two or more groups of magnetic particles, wherein the two or more groups of magnetic particles differ from each other with respect to e.g. with respect to size, capture sites number and/or type.

In an embodiment of the invention where the method comprises quantitative or qualitative determination of two or more target components in a liquid sample, the magnetic particle comprises one or more types of capture sites for the two or more target components, the capture sites for one target component preferably differs from the capture sites for another target component. For example one group of magnetic particles can comprise one type of capture sites and another group of magnetic particles can comprise another type of capture sites.

The plurality of fluorophores may e.g. comprise at least one group of fluorophores configured to bind to one capture site for one target component and at least another group of fluorophores configured to bind to the capture site for another target component.

By a few examples and based on the teaching herein the skilled person can find suitable fluorophores and magnetic particles for a given test according to the method of the invention.

In a preferred embodiment of the invention, the method comprises performing two or more parallel assays on the liquid sample for quantitative or qualitative determination of the target component(s), each assay comprises bringing a part of the liquid sample into contact with the fluorophores and the magnetic particles in a micro fluidic device comprising a transparent window; and at least temporally immobilizing the magnetic particles adjacent to the transparent window using a magnet, emitting exciting electromagnetic beam(s) towards the immobilized magnetic particles, reading signals emitted from fluorophores captured by the immobilized magnetic particles.

Preferably the fluorophores used in one of the two or more parallel assays differ from the fluorophores used in another one of the two or more parallel assays.

For example the fluorophores used in one of the two or more parallel assays differ from the fluorophores used in another one of the two or more parallel assays with respect to types, sizes, coatings, shape and/or amounts.

In an embodiment of the invention the magnetic particles used in one of the two or more parallel assays differ from the magnetic particles used in another one of the two or more parallel assays. For example the magnetic particles used in one of the two or more parallel assays differ from the magnetic particles in another one of the two or more parallel assays with respect to types, sizes, coatings, shape and/or amounts.

In an embodiment the two or more parallel assays are performed simultaneously in the same micro fluidic device. The two or more parallel assays may e.g. be performed in respective flow channels, such as in parallel flow channels of the same micro fluidic device.

In an embodiment of the invention, the quantitative or qualitative determination of target component(s) in a liquid sample is performed by comparing the read signal(s) with a reference schedule.

The reference schedule can be any type of reference schedule which can be applied for calibrating the read signal, for example such as it is generally known in the art.

In an embodiment of the invention, the quantitative or qualitative determination of target component(s) in a liquid sample is performed by comparing the read signal(s) with signals obtained from liquid samples with a known composition, e.g. by using an artificial intelligent processor.

In an embodiment of the invention, the quantitative or qualitative determination of target component(s) in a liquid sample is performed by multiplexing the read signal(s) from different groups of fluorophores e.g. from the same assay, from fluorophores from parallel assays and/or from fluorophores in reference tests of known or unknown liquid samples.

The invention also comprises a system for quantitative or qualitative determination of a target component in a liquid sample.

The system of the invention for quantitative or qualitative determination is specifically suitable for use for performing the method of the invention, and accordingly the system for quantitative or qualitative determination and embodiments thereof has at least some of the above mentioned benefits.

The system for quantitative or qualitative determination of a target component in a liquid sample comprises a micro fluidic device comprising at least one flow channel with a transparent window and an inlet for the liquid sample;

a plurality of magnetic particles comprising one or more capture sites for the target component on their respective surfaces;

a plurality of fluorophores configured to bind to the capture sites of the magnetic particles;

a magnet arranged to at least temporally immobilize the magnetic particle adjacent to the transparent window;

an emitter for exciting the fluorophores, and a reader for reading signals emitted from the fluorophores.

Advantageously the micro fluidic device is as described elsewhere herein. The magnetic particles, the fluorophores and the magnet may e.g. be as described above.

In an embodiment the micro fluidic device is of polymer and or glass.

In an embodiment the micro fluidic device comprises a substrate with a groove for the flow channel and a foil covering the flow channel.

The micro fluidic device comprises preferably an excitation and read out zone which is also referred to as a reading zone and which is provided in the form of the transparent window, which is preferably transparent for at least the excitation and emitting wavelengths of the fluorophores.

In an embodiment the excitation and read out zone is identical to a zone where the magnet is positioned when it is acting on the magnetic particle to immobilize the magnetic particles. After the magnetic particles have been immobilized using the magnet and any liquid in the flow channel is at standstill, the magnet is removed while the magnetic particles remain immobilized at least for a sufficient time to excite the fluorophore and read the signal emitted from the fluorophore.

The emitter and the reader are advantageously a common emitter and reader unit.

In an embodiment the emitter comprises emitting optical fibers comprising output ends and the receiver comprises one or more receiver optical fibers comprising input ends. Advantageously fiber sections comprising the optical fiber output ends of the emitter and fiber sections comprising the optical fiber input ends of the reader are connected to each other to form a common emitting-reading fiber bundle. The output ends of the emitting optical fibers and the input ends of the receiver optical fibers are advantageously arranged in a pattern e.g. as described above.

The flow channel of the micro fluidic device may in principle have any shape. In an embodiment the flow channel comprises an elongate flow section and one or more chamber sections (chamber sections that have a substantially larger cross-section than the flow section). The fluorophores and the magnetic particles may for example be temporally immobilized in such chamber sections.

In an embodiment of the system of the invention for quantitative or qualitative determination the micro fluidic device is of polymer and or glass or a combination thereof. In a preferred embodiment the micro fluidic device is of polymer. The polymer micro fluidic device is easy and cost-effective to produce. The micro fluidic device preferably comprises a substrate with a groove for the flow channel and a foil covering the flow channel.

In an embodiment the micro fluidic device comprises an inlet to the flow channel. The inlet is for example an opening for suction, a capillary inlet or a membrane covered inlet.

In an embodiment of the invention the inlet of the micro fluidic device is a membrane covered inlet. In this embodiment the liquid sample can for example be introduced into the flow channel using a syringe or similar needle assisted device which can be used to penetrate the membrane. The membrane may e.g. simultaneously provide an escape for gas in the flow channel.

In an embodiment of the invention the inlet of the micro fluidic device is a capillary inlet, meaning that the liquid sample can be drawn into the flow channel using capillary forces. In this embodiment it is desired that the inner surfaces of the flow channel, in particular adjacent to the inlet, have a relatively high surface tension and have sufficiently small dimensions for providing the capillary forces. It is well known in the art to provide micro fluidic devices with a capillary inlet. Most polymers have a relatively low surface tension and often it is required to treat the surface of polymer micro fluidic device where the inner surfaces of the flow channel should provide capillary forces for a liquid e.g. an aqueous liquid.

In an embodiment of the invention the inlet of the micro fluidic device is an opening for suction, i.e. the micro fluidic device is configured such that the liquid sample is adapted to be sucked into the flow channel. In this embodiment the inner surfaces of the flow channel need not provide capillary forces and even when the micro fluidic device is of a material with a low surface tension, such surface need not be treated for increasing the surface tension. The micro fluid device with a suction inlet is therefore very simple to produce and can be provided at relatively low cost.

In an embodiment of the invention the micro fluidic device comprises an inlet for suction in the liquid sample. Advantageously the micro fluidic device comprises a flexible wall section and the system can beneficially comprise an actuator, where the actuator is arranged to move the flexible wall section. The actuator is e.g. a step motor driven actuator.

In an embodiment of the invention where system comprises an actuator and where the inlet of the micro fluidic device comprises a flexible wall section and the inlet is an opening for suction, the inlet and the actuator are arranged such that the upon activation of the actuator, the flexible wall section will be moved and air will be pressed out of the flow channel where after the flexible wall will return to its initial position and the liquid sample will be sucked into the flow channel. Thereby a simple and effective suction of the liquid sample into the flow channel and a simple and effective mixing of the sample with the fluorophores and magnetic particles can be obtained.

In an embodiment of the invention the micro fluidic device comprises a sink section and the flow channel is in fluid communication with the sink section.

The sink section of the micro fluidic device is a section which is applied in a distance from the transparent window where the magnetic particle is at least temporally immobilized for excitation and read out. The sink section is in an embodiment applied to collect the sample or most of the sample during or after the test has been completed. By collecting the sample or most of the sample while simultaneously immobilizing the magnetic particles adjacent to the transparent window for excitation and read out, the risk of obtaining false signals due to fluorophores in the sample can be highly reduced.

Advantageously the sink section is positioned remotely to the inlet to the flow channel. Preferably the fluid introduced via the inlet must pass the transparent window where the magnetic particle is at least temporally immobilized for excitation and read out before the liquid reaches the sink section.

The terms "sink" and "sink section" are used interchangeably

The flow channel may have any shape and is preferably adapted for performing determinations on relatively small volumes of liquid sample, such as from about 1 µl to about 1 ml, preferably from about 5 µl to about 0.5 ml. The flow channel can have any shape e.g. with a cross sectional shape selected from round, ellipsoidal, semi ellipsoidal, quadrilateral polygonal, square, rectangular and trapezoidal shapes, where any edges optionally being rounded. In one embodiment the microfluidic device comprises two or more distinct flow channel sections, e.g. a channel section for mixing the liquid sample with the fluorophores and/or the magnetic particles and a channel section with a transparent window for at least temporally immobilizing the magnetic particles for excitation of optional captured fluorophores and for reading out possible emission energy.

In an embodiment of the invention the microfluidic device comprises at least one gas escape opening for allowing gas to escape from the flow channel. The gas escape opening may be of any type and shape e.g. as known from prior art microfluidic devices. The gas escape opening may for example be arranged to allow gas to escape completely out of the microfluidic device or it may allow the gas to escape into a gas collecting chamber e.g. in the form of an inflatable unit.

In an embodiment of the invention the microfluidic device comprises a flexible wall section which can be used to create a suction at the inlet of the flow channel. In this embodiment the inlet can function as a gas escape opening.

In an embodiment the micro fluidic device comprises two or more flow channels, and the two or more flow channels comprise a common section or are in fluid connection with a common sink section, where the common section or the common sink section comprises a flexible wall section which can be used to create a suction at the inlets of the flow channels.

In an embodiment the micro fluidic device comprises two or more flow channels, and the two or more flow channels or one or more sink sections in fluid connection comprise each a flexible wall section which can be used to create a suction at the respective inlets of the flow channels. In this embodiment suction can be applied individually in the respective flow channels. The flexible wall section is in an embodiment applied as a wall section of a sink section where the sample or parts thereof can be collected after performing the test. The sink section is e.g. as described above.

In an embodiment the flexible wall section is used to pump out the sample after the magnetic particles have been mixed with the sample and the fluorophores while simultaneously immobilizing the magnetic particles adjacent to the transparent window for excitation and read out, thereby reducing the risk of obtaining false signals due to fluorophores remaining in the sample.

In an embodiment where the micro fluidic device comprises a flow channel in fluid connection with a sink for collecting sample and optionally a flexible wall suitable for pumping the sample into and out of the sink, a sample modifier such as a surfactant is applied in the sink. When the sample is pumped into the sink using the flexible wall section or other pumping means the sample will be intermixed with the surfactant and accordingly the surface tension of the sample is reduced. By reintroducing the sample into the area of the flow channel comprising the transparent window, the magnetic particles immobilized adjacent to the transparent window will be washed with the modified sample. The modifier applied in the sink may e.g. be in a dry form such that it will not be mixed with the sample until the sample is introduced into the sink.

In an embodiment the flexible wall section is used to pump out the sample after termination of the test. Whether it is preferred to collect the sample in the sink section, to pump out the sample or to let the sample be distributed in the flow channel depends largely on the kind and the toxicity of the sample applied. If for example there is risk of undesired contamination or if the sample potentially comprises elements that are undesirable to spread e.g. bacteria, viruses or similar, it may be desired to collect the sample in the sink section during or after performing the test.

In an embodiment the flow channel of the micro fluidic device comprises one or more chambers, e.g. for mixing the liquid sample with the fluorophores and/or the magnetic. In general it is desired that the flow channel comprises at least one liquid flow channel section which has at least one dimension (often the width dimension) of at least about 100 µm, such as at least 500 µm. In practice it can be as wide as handling will allow. The other dimension(s), e.g. the depth of the channel, is preferably smaller than the width, such as half the width or e.g. down to about 25 µm or down to about 10 µm, if desired.

In this context a chamber of a flow channel means a subsection of the flow channel that has at least 25%, such as at least 50%, larger cross-sectional area than an adjacent section of the flow channel. The chamber may for example have a larger cross sectional area than an adjacent channel section by being wider. The depth of the flow channel may be substantially constant or it may vary.

In an embodiment of the system of the invention for quantitative or qualitative determination, the micro fluidic device comprises an excitation and read out zone in the form of a length section comprising the transparent window, the window is transparent for at least the exciting and emitting wavelengths of the fluorophores.

In an embodiment of the system of the invention for quantitative or qualitative determination, the micro fluidic device comprises an excitation and read out section that has a length dimension of at least about 1 mm, such as at least about 3 mm, such as at least about 5 mm.

The read out section is preferably formed as a narrowed part of the flow channel or as an expanded part of the flow channel in order to provide a simple positioning of the micro fluidic device in relation to the emitter and reader.

According to the system of the invention at least the window of the micro fluidic device is of a transparent material.

In an embodiment the whole flow channel is visible due to transparency of the material. In an embodiment the whole micro fluidic device is of a transparent material In a preferred embodiment at least the transparent window is transparent to the exciting wavelength(s) and emitting wavelength(s) of the fluorophores. In an embodiment at least the transparent window is transparent to at least one wavelength selected from Infrared light (about 700 nm to about 1000 µm), visible light (about 400 nm to about 700 nm), UV light (about 400 nm to about 10 nm) about and X-ray light (about 10 nm to about 0.01 nm).

It is in an embodiment desired to apply short wave light for the determination, i.e. the fluorophores are preferably excitable by short wavelength energy where the heat generation is relatively small and will not interfere with the determination.

Examples of materials which may be used for the micro fluidic device comprise materials selected from glass and polymer, preferably polymers selected from cyclic olefin copolymers (COC), acrylonitrile-butadiene-styrene copolymer, polycarbonate, polydimethyl-siloxane (PDMS), polyethylene (PE), polymethylmethacrylate (PMMA), polymethylpentene, polypropylene, polystyrene, polysulfone, polytetra-fluoroethylene (PTFE), polyurethane (PU), polyvinylchloride (PVC), polyvinylidene chloride (PVDC), polyvinylidine fluoride, styrene-acryl copolymers polyisoprene, polybutadiene, polychloroprene, polyisobutylene, poly(styrene-butadiene-styrene), silicones, epoxy resins, Poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN) polyamide (PA), polyamide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), and mixtures thereof.

In an embodiment the micro fluidic device is provided from a base part of a rigid material—e.g. produced by injection molding or by laser carving in a substrate. The base part is covered with a foil which is bonded to the base part to form the flow channel and optionally sink section.

In an embodiment of the invention the micro fluidic device comprises two or more flow channels optionally for performing parallel tests, the two or more flow channels optionally have a common inlet.

In an embodiment of the system of the invention for quantitative or qualitative determination, the system comprises a temperature regulator for regulating the temperature of the liquid sample in the flow channel. For some tests the reaction between possible target component and capture sites is temperature sensitive and accordingly it can be desirable to regulate the temperature. The temperature regulator can for example comprise a peltier element, a thin film heating element and/or other resistive heating elements.

In an embodiment of the system of the invention for quantitative or qualitative determination, the magnetic particles are coated magnetic particles comprising a coating comprising the captures sites, wherein the capture sites are selected to be capture sites for the target component, such as a biomolecule.

In an embodiment of the system of the invention for quantitative or qualitative determination, the fluorophores are quantum dots or aromatic probes and/or conjugated probes, the fluorophores are preferably quantum dots.

In an embodiment of the system of the invention for quantitative or qualitative determination, the fluorophores are configured to bind to the capture sites of the magnetic particles by being coupled to a component which can bind to the capture sites of the magnetic particles, the component is preferably identical or homolog to the target component.

In an embodiment of the system of the invention for quantitative or qualitative determination, the fluorophores and the magnetic particles are temporally immobilized in the flow channel of the micro fluidic device of the micro fluidic device such that they cannot bind to each other prior to the feeding of a liquid sample to the flow channel.

In an embodiment of the system of the invention for quantitative or qualitative determination, the magnet is arranged to at least temporally immobilize the magnetic particle adjacent to the transparent wall section for a sufficient time to excite at least a part of possible fluorophores captured by the capture sites of the magnetic particles by the emitter and to read out possibly emitted signal from possibly captured fluorophores.

Emitters and readers for electromagnetic waves are well known in the art, and when the fluorophores have been selected the skilled person will in a simple manner be able to select an emitter and reader that are useful in combination with the fluorophores.

In an embodiment of the system of the invention for quantitative or qualitative determination, the emitter is a light emitting diode or a laser which is capable of emitting electromagnetic radiation comprising the exciting wavelength of the fluorophores.

In an embodiment of the system of the invention for quantitative or qualitative determination, the emitter is configured to emit electromagnetic radiation directed at the transparent window, the window has a planar surface, the emitter is preferably configured to emit electromagnetic radiation directed at the transparent window with an angle to the surface of the window which is from about 20° to about 170°, such as from about 30° to about 150°. Preferably the surface of the window is substantially plane in order to optimize the exciting and emitting functions.

In an embodiment of the system of the invention for quantitative or qualitative determination, the reader is configured for reading signals emitted from fluorophores captured by magnetic particles which are temporally immobilized adjacent to the window.

The emitter and the reader are advantageously a common emitter and reader unit.

In an embodiment the emitter comprises emitting optical fibers comprising output ends and the receiver comprises one or more receiver optical fibers comprising input ends. Advantageously fiber sections comprising the optical fiber output ends of the emitter and fiber sections comprising the optical fiber input ends of the reader are connected to each other to form a common emitting-reading fiber bundle. The output ends of the emitting optical fibers and the input ends of the receiver optical fibers are advantageously arranged in a pattern e.g. as described above.

In an embodiment of the system of the invention for quantitative or qualitative determination, the system comprises a computer for performing the quantitative or qualitative determination of target component(s) in a liquid sample based on the read signal(s). The computer is preferably programmed to perform a quantitative and/or qualitative determination of the target component in the liquid sample based on the read signal.

In an embodiment the computer comprises a memory for storing of read signal(s) and/or quantitative or qualitative determinations performed.

In an embodiment the computer comprises a memory, which memory comprises a reference schedule for comparing the read signal(s) to perform the determination. The reference schedule may preferably comprise sets of a quantitative or qualitative determination with read signal(s), for example a set of data comprises a) the result(s) of read signal(s) for a liquid sample with a known content of the target component and b) the known content of the target component.

In an embodiment the computer is an artificial intelligent processor, programmed to compare read signal(s) with stored signals obtained from liquid samples with known compositions.

In an embodiment the system comprises a signal processor comprising the computer wherein the signal processor is configured to multiplex signals from different groups of fluorophores, from fluorophores from parallel assays and/or from fluorophores in reference tests of known or unknown liquid samples.

In an embodiment the system comprises a signal processor comprising the computer wherein the signal processor is configured to multiplex signals from different groups of fluorophores applied in same assay.

Multiplexing of signals is well known in the art and has also been applied in the art of analyzing test samples to quantify two or more targets labeled with fluorophores emitting different wavelengths. Reference is made to for example US 2009/0270269 and WO 2010/141105 and further information about multiplexing can also be found in "Luminescent quantum dots for multiplexed biological detection and imaging" Chan et al. Current Opinion in Biotechnology 2002, 13:40-46, Elsvier Science.

When performing the quantitative or qualitative determination using multiplexing it is preferred that the fluorophores applied are quantum dots. According to the invention it has been found that by using quantum dots as fluorophores and multiplexing the signals it is possible to quantitatively determine a plurality of target components simultaneously, e.g. 10 or more or even 50 or more.

The emitter, the reader and the signal processor comprising the computer are advantageously in form of a common or at least interconnected unit.

The invention also relates to a kit for preparing a liquid sample for being analyzed by the method of the invention as described above.

The kit of the invention is adapted for preparing a liquid sample for optical analysis for quantitative or qualitative determination of a plurality of target components in the sample. The kit comprises a plurality of magnetic particles comprising a type of capture sites for each of the target components on their surfaces; and a plurality of groups of fluorophores, each group of fluorophores is configured to bind to one of the types of capture sites of the magnetic particles.

The magnetic particles and the groups of fluorophores are as described above.

In an embodiment where the kit for preparing a liquid sample for optical analysis for quantitative or qualitative determination of N different target components in the sample, where N is an integer of 2 or more, the kit comprises a plurality of magnetic particles comprising N types of capture sites, one type of capture sites for each of the target components; and N groups of fluorophores, each group of fluorophores is configured to bind to one of the types of capture sites of the magnetic particles.

In an embodiment where the kit for preparing a liquid sample for optical analysis for quantitative or qualitative determination of N different target components in the sample, where N is an integer of 2 or more, the kit comprises N groups of magnetic particles, each group of magnetic particles comprises one type of capture sites for one target component; and N groups of fluorophores, each group of fluorophores is configured to bind to one of the types of capture sites of the magnetic particles;

In an embodiment two or more groups of fluorophores are provided in one single solution. The magnetic particles are advantageously provided in the form of one solution or suspension for simple handling.

The two or more groups of fluorophores are as described above and preferably the two or more groups of fluorophores are quantum dots capable of being excited by electromagnetic waves of the same wavelength.

In an embodiment the kit further comprises a micro fluidic device and/or a magnet. The micro fluidic device and/or magnet can for example be as described above.

In principle N can be as high as the number available of different fluorophores such as quantum dots. In an embodiment N is an integer from 2 to 10.

The invention also relates to a micro fluidic device for use in preparing a liquid sample for optical analysis for quantitative or qualitative determination of a of target component in the sample. The micro fluidic device comprises at least one flow channel with a transparent window and an inlet for the liquid sample, the micro fluidic device further comprises in its flow channel a plurality of magnetic particles comprising capture sites for the target component on their surfaces; and a plurality of fluorophores configured to bind the capture sites of the magnetic particles.

The micro fluidic device is preferably a micro fluidic device as described above.

The invention further relates to a micro fluidic device for use in preparing a liquid sample for optical analysis for quantitative or qualitative determination of a of target component in the sample which micro fluidic device comprises a substrate with a groove for a flow channel and a foil covering the flow channel, the flow channel comprises a transparent window and an inlet for suction in the liquid sample. The micro fluidic device comprises a flexible wall section of the flow channel or of a sink section in fluid connection with the flow channel. The flexible wall section can be moved such that air will be pressed out of the flow channel where after the flexible wall will return to its initial position.

In an embodiment of the invention the micro fluidic device comprises a sink section and the flow channel is in fluid communication with the sink section.

The sink section of the micro fluidic device is a section which is applied in a distance from the transparent window where the magnetic particle is at least temporally immobilized for excitation and read out. The sink section is in an embodiment applied to collect the sample or most of the sample during or after the test has been completed. Advantageously the sink section is positioned remotely to the inlet to the flow channel.

Further preferred embodiments of the micro fluidic device are as described above.

In an further aspect a modification of the invention relates to a sandwich-type assay for quantitative or qualitative determination of a target component in a liquid sample. The assay comprises providing a plurality of magnetic particles comprising one or more capture sites for the target component on their respective surfaces;

providing a plurality of fluorophores comprising one or more capture sites for the target component;

bringing the liquid sample, said fluorophores and said magnetic particles into a flow channel of a micro fluidic device comprising a transparent window into the flow channel; and at least temporally immobilizing said magnetic particles adjacent to said transparent window using a magnet, emitting exciting electromagnetic beam towards said immobilized magnetic particles, reading signals emitted from fluorophores captured by said immobilized magnetic particles via said target components and performing a quantitative or qualitative determination of said target component based on the read signal.

The magnetic particles are advantageously as described above.

The fluorophores are advantageously as described above with the modification that the fluorophores are not configured to bind to the capture sites of the magnetic particle, but instead the fluorophores comprise one or more capture sites for the target component.

The liquid sample, the fluorophores and the magnetic are advantageously brought into contact using the methods described above.

The micro fluidic device is advantageously as described above.

The at least temporally immobilizing of the magnetic particles, the exciting and read out are advantageously as described above.

The sandwich-type assay is specifically advantageous to use where the target component is a relatively large component comprising two or more capture sites such that it can be sandwiched between the magnetic particle and the fluorophore.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there are specific reasons for not combining such features.

BRIEF DESCRIPTION OF DRAWINGS AND EXAMPLES

The invention will be explained more fully below in connection with examples and preferred embodiments and with reference to the drawings in which.

The figures are schematic and may be simplified for clarity. Throughout, the same reference numerals are used for identical or corresponding parts.

Figure 1A:
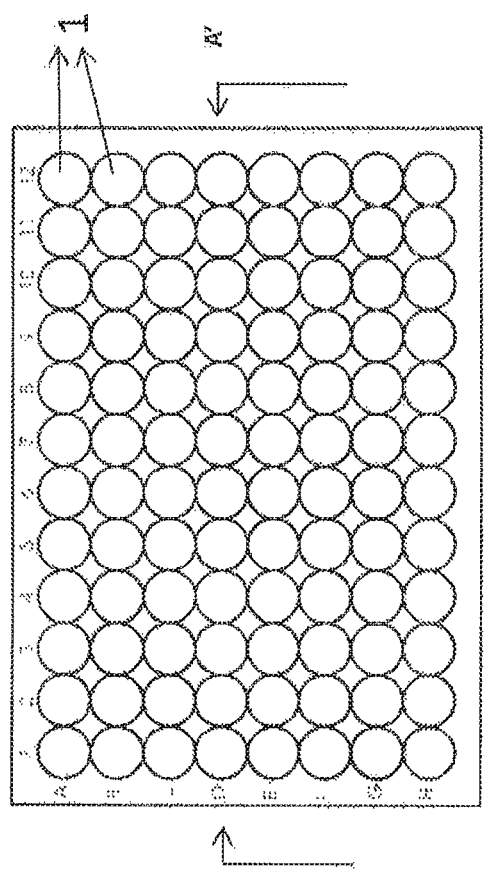
FIG. 1a is a schematic top view of a micro titer plate suitable for performing the method of the invention.
Figure 1B:
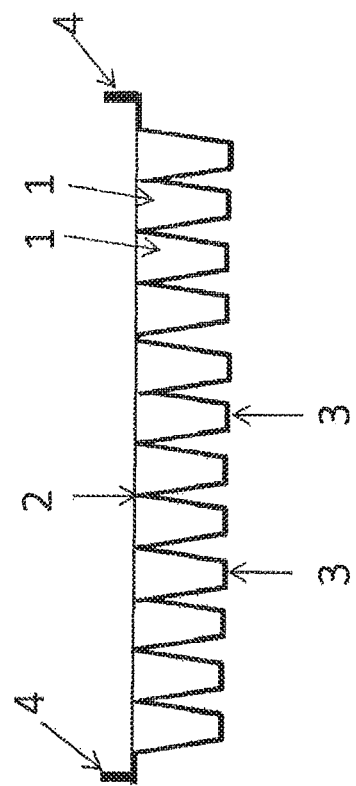
FIG. 1b is a schematic cross sectional view seen in the line A-A' of FIG. 1.

FIGS. 1a and 1b show a test plate suitable for being applied in the present invention. The shown test plate is a micro titer plate with 12×8 wells 1.

Figure 9:
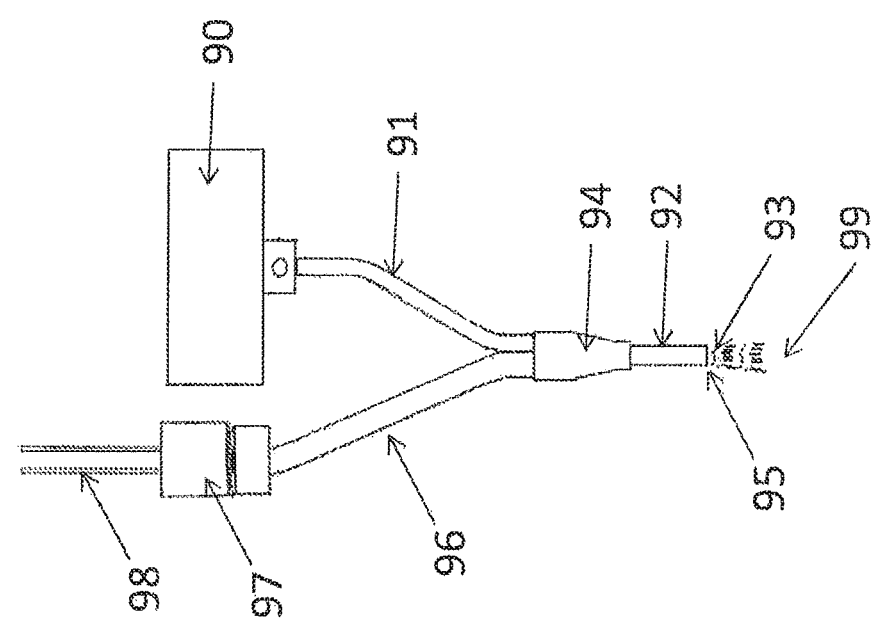

FIG. 9 is a schematic side view of an emitter-reader assembly.

Micro titer plates are well known in the art under many names, such as well plates and micro plates. A micro titer plate is a generally flat plate with multiple "wells" used as small test tubes. The shown micro titer plate comprises a thin cover film 2, which is peeled of prior to use of the titer plate. The cover film 2 can be divided into sections, such that it can be peeled off in sections, e.g. such that only one or only a number less than all wells are uncovered by removal of a section of the cover film 2. The micro titer plate has an edge 4 for reducing spill.

Each well 1 of a micro plate typically holds somewhere between tens of nanoliters to several milliliters of liquid. Wells of a suitable micro titer plate can in principle have any shape, such as circular or square, and their respective bottom parts can be rounded or plane. In the shown micro titer plate, the wells 1 are round and with plane bottom parts 3. The round bottom parts 2 of the respective wells 1 constitute the transparent window usable for exciting and reading out. In use the fluorophores and the magnetic particles can be pre-arranged in the wells e.g. in dry form and e.g. in temporally immobilized form. Alternatively the fluorophores and the magnetic particles can be added to the well immediately before, simultaneously with or after adding the liquid sample. After a selected incubating time e. g. on a shaking board, the micro titer plate is placed on a magnet for temporally immobilizing the magnetic particles adjacent to the transparent window, namely at the bottom part 3. An emitter is arranged to emitting exciting electromagnetic beam towards the immobilized magnetic particles, and a reader is arranged to read signals emitted from fluorophores captured by the immobilized magnetic particles. The read signals are used to perform a quantitative or qualitative determination of the target component. For reducing noise, the liquid can be removed from the respective wells, and optionally the wells are washed e.g. with water prior to reading out signals. The incubating time is usually very short e.g. a few minutes.

Figure 2:
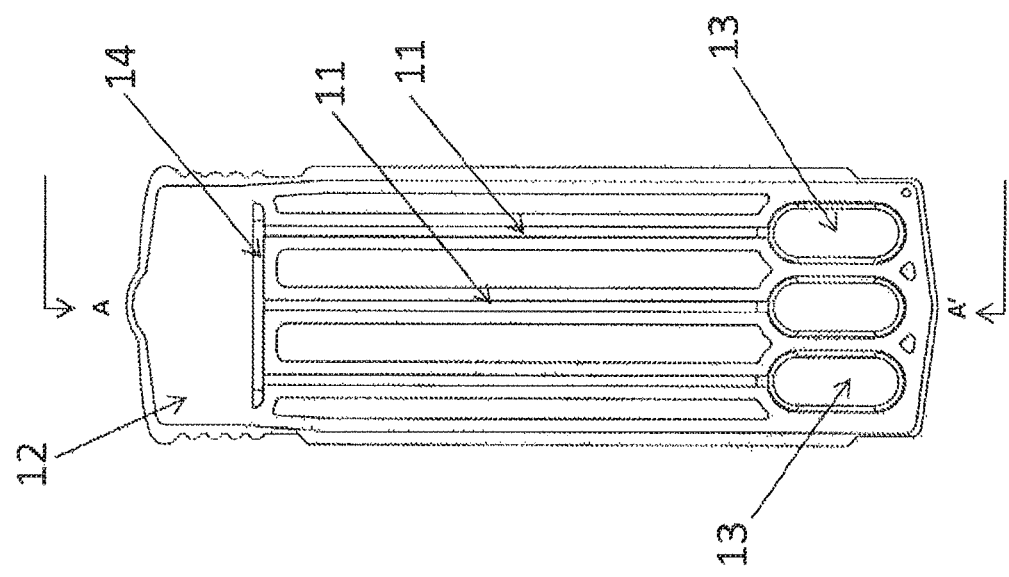
FIG. 2 is a schematic top view of a micro fluidic device suitable for performing the method of the invention.
Figure 3:
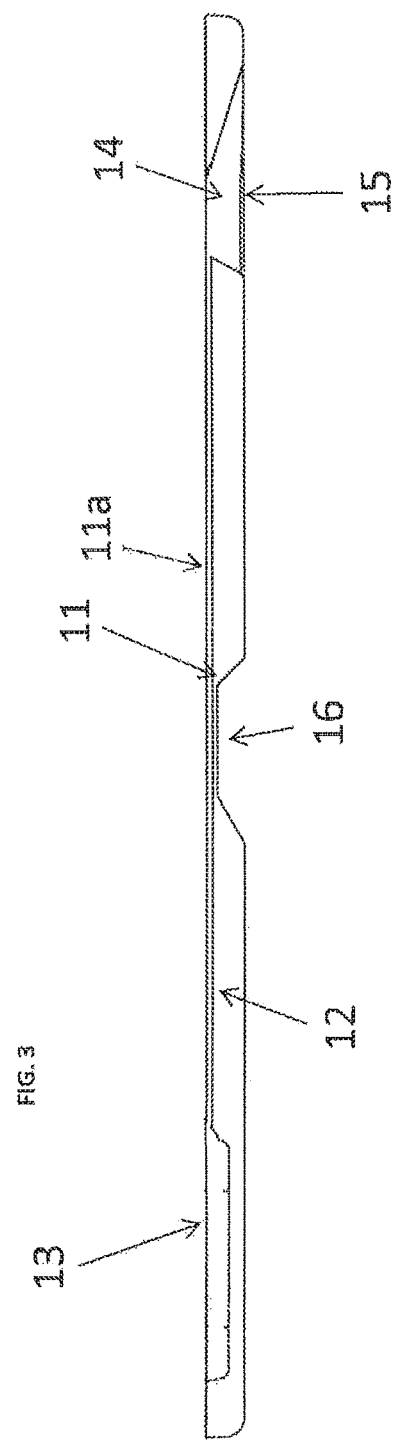
FIG. 3 is a schematic sectional side view seen in the line B-B' of FIG. 2.

FIGS. 2 and 3 show a test plate suitable for being applied in the present invention. The shown test plate is a micro fluidic device. Although any micro fluidic devices in principle could be applied in the present invention, the micro fluidic device shown is particularly designed for the purpose and provides additional benefits to the present invention as described herein.

The micro fluidic device comprises a substrate 12 with three flow channels 11. The channels 11 are provided in the form of grooves covered with a foil 11a. Each channel 11 comprises an inlet 13 and the channels 11 is in fluid connection with a common sink 14.

The inlet 13 is in the form of a well shaped inlet.

The common sink 14 of the micro fluidic device comprises a flexible wall section 15. The flexible wall section 15 can be moved e.g. using a not shown actuator as described above.

By pressing the flexible wall section 15 it will be moved and air will be pressed out of the channels 11 where after the flexible wall section 15 will return to its initial position and a liquid sample arranged in the inlet will be sucked into the channel to a desired position. By further manipulating the flexible wall section the liquid sample can be drawn further into the channels 11 or it can be pulsated in the channels. Finally the flexible wall section 15 can be manipulated to collect the sample in the sink and to reflush the sample into the channels, if desired. The flexible wall section 15 thereby provides a simple and cheap method of controlling the liquid sample in the micro fluidic device.

The micro fluidic device also comprises an indent which provides a read out section 16 for the channels 11. In the read out sections 16 of the channels 11, the channels comprise a transparent window and the magnetic particles can be temporally immobilized using a not shown magnet.

Figure 4:
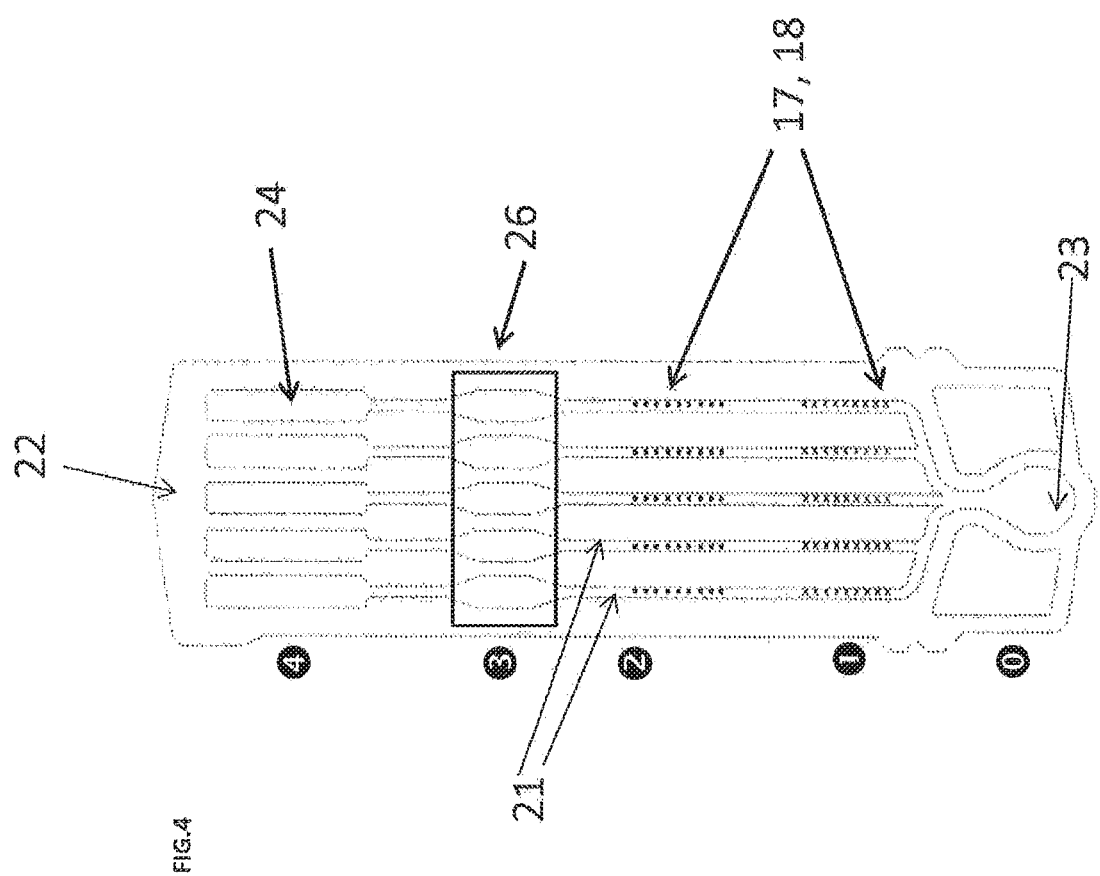
FIG. 4 is a schematic top view of micro fluidic device suitable for performing the method of the invention and with temporally immobilized magnetic particles and temporally immobilized fluorophores.

FIG. 4 shows another preferred micro fluidic device suitable for use in the invention.

The micro fluidic device comprises a substrate 22 with five flow channels 21. Each channel 21 comprises an inlet 23 and is in fluid connection with a sink 24 with a not shown flexible wall section.

The micro fluidic device also comprises an indent which provides a read out section 26 for the channels 21, where the channels comprise a transparent window and the magnetic particles can be temporally immobilized using a not shown magnet.

Each channel 21 comprises temporally immobilized magnetic particles and temporally immobilized fluorophores. The micro fluidic device is divided into zones comprising zone 0 which is the inlet zone, zone 1 and zone 2 which comprise temporally immobilized fluorophores and magnetic particles 17 arranged such that they do not react until they are in contact with the liquid sample, zone 3 which is the read out zone and zone 4 which is the sink zone.

In an embodiment zone 1 comprises temporally immobilized fluorophores and zone 2 comprises temporally immobilized magnetic particles.

In an embodiment zone 1 comprises temporally immobilized magnetic particles and zone 2 comprises temporally immobilized fluorophores.

The micro fluidic device could comprise several subzones of zone 1 and zone 2, if desired.

In use the liquid sample is fed to the inlet 23, the sample is sucked into zone 1 of the channels using the flexible wall section. Optionally the liquid sample is pulsated in zone 1 to dissolve or resuspend the immobilized elements 17 in zone 1. Thereafter the liquid sample is drawn further into the channels 21 to zone 2 for dissolving or resuspending the immobilized elements 17 in zone 2. After a preselected incubation time the liquid sample is drawn fully into the sinks 24. The magnetic particles are immobilized in the read out zone 3. If desired, the liquid sample can be reintroduced into the channels 21 by using the flexible wall of the sinks 24 and the immobilized magnetic particles can be flushed using the liquid sample to remove not immobilized fluorophores and other elements that could potentially provide noise.

Figure 5:
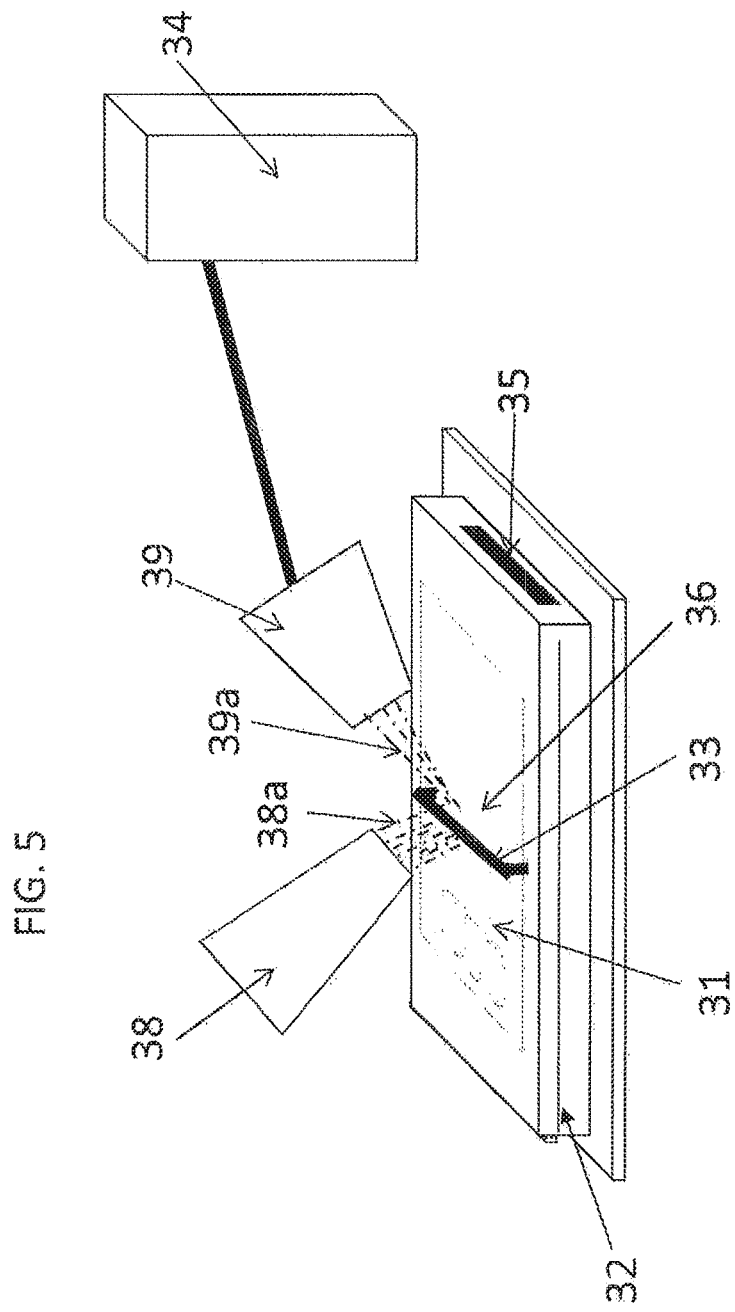
FIG. 5 is a schematic illustration of the system of the invention comprising a micro fluidic device, an emitter and a reader.

FIG. 5 shows a system of the invention comprising a support element 32 supporting a micro fluidic device 31, an emitter 38 and a reader 39 coupled to a computer 34. The micro fluidic device comprises a read out section 36. The support element 32 comprises a temperature control element 35 for maintaining the liquid sample at a desired temperature during the test. The support element 32 further comprises a magnet 33. The micro fluidic device is arranged such that the magnet is located adjacent the read out section 36 to thereby temporally immobilize the magnetic particles in the read out section 36. The emitter 38 is configured to emit electromagnetic radiation directed at the read out section 36 to thereby excite fluorophores on the immobilized magnetic particles. The reader 39 is configured to read signals emitted from fluorophores captures by the immobilized magnetic particles and the read signals are transmitted to the computer 34 for processing to quantitative and/or qualitative determination of target compound(s).

Figure 6:
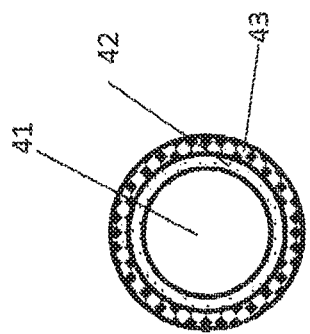
FIG. 6 is a schematic illustration of a fluorophore in the form of a quantum dot suitable for use in the invention.

FIG. 6 shows a fluorophore in the form of a quantum dot suitable for use in the invention. The quantum dot comprises a core 41 of a binary semiconductor alloy covered by a transparent shell 42 which is at least transparent for the wavelength emitted by the core. The shell 42 is further covered by an organic coating 43, such as a polymer coating which is coupled to one or more not shown components which can bind to the capture sites of the magnetic particles e.g. such as described above.

Figure 7:
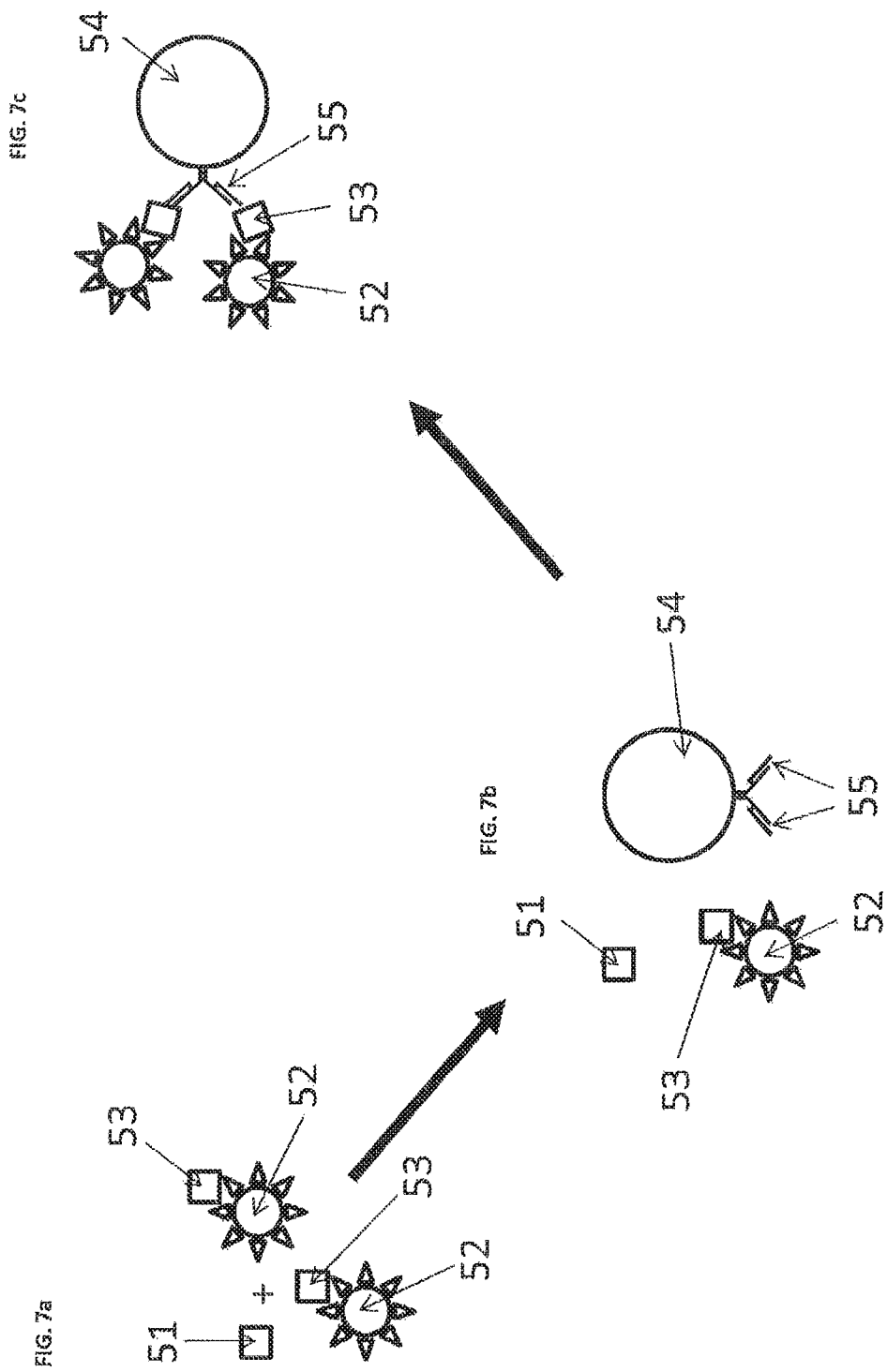
FIGS. 7a, 7b and 7c are schematic illustrations of a performance of the method of the invention.

FIGS. 7a, 7b and 7c show a performance of the method of the invention in three steps. Step 1 is illustrated in FIG. 7a. Sample with the target component 51 is mixed with fluorophores 52 coupled to homologue target component 53. The relative amount of target component 51 to fluorophores 52 coupled to homologue target component 53 is relatively low. Step 2 is illustrated in FIG. 7b. The mixture of target component 51 and fluorophores 52 coupled to homologue target component 53 is further mixed with magnetic particles 54 carrying capture sites 55 for the target component 51 and the homologue target component 53. Step 3 is illustrated in FIG. 7c. Target component 51 and the homologue target component 53 are captured by the capture sites 55 carried by the magnetic particles 54. In the illustration shown, only the homologue target component 53 is captured by the capture sites 55. This is shown to illustrate that the amount of captured homologue target component 53 is relatively high and accordingly the amount of immobilized fluorophores 52 is relatively high. When the magnetic particles 54 are immobilized using a magnet arranged adjacent to the transparent window, and the fluorophores 52 are excited, the emitted signal from the fluorophores 52 is relatively high, and the amount of target component 51 can be determined.

Figure 8:
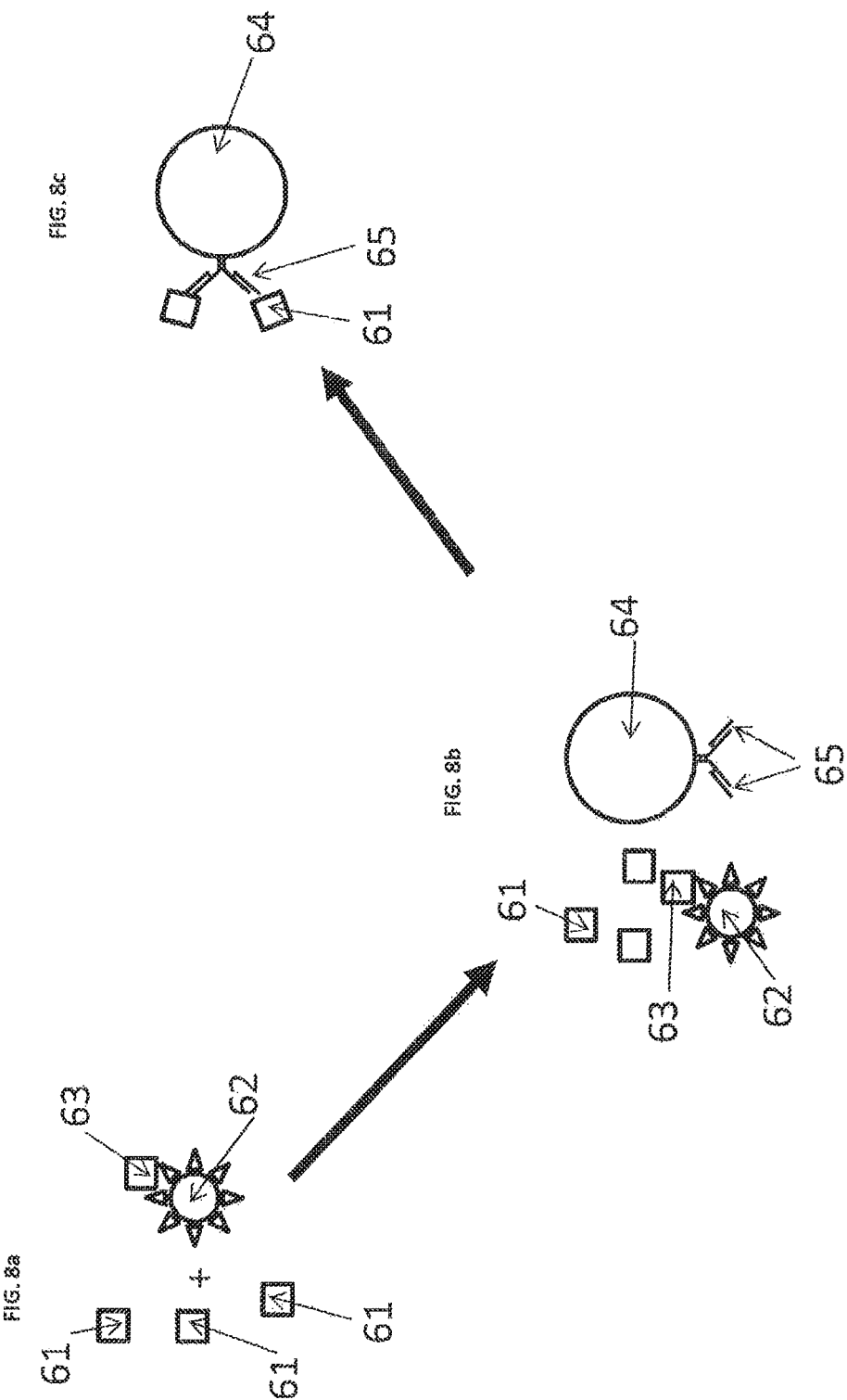
FIGS. 8a, 8b and 8c are schematic illustrations of another performance of the method of the invention.

FIGS. 8a, 8b and 8c show another performance of the method of the invention in three steps. Step 1 is illustrated in FIG. 8a. Sample with the target component 61 is mixed with fluorophores 62 coupled to homologue target component 63. The relative amount of target component 61 to fluorophores 62 coupled to homologue target component 63 is relatively high. Step 2 is illustrated in FIG. 8b. The mixture of target component 61 and fluorophores 62 coupled to homologue target component 63 is further mixed with magnetic particles 64 carrying capture sites 65 for the target component 61 and the homologue target component 63. Step 3 is illustrated in FIG. 8c. Target component 61 and the homologue target component 63 are captured by the capture sites 65 carried by the magnetic particles 64. In the illustration only the target component 61 captured by the capture sites 65 is shown to illustrate that the amount of captured target component 61 is relatively high and accordingly the amount of immobilized fluorophores 62 is relatively low or there may be none at all and when the magnetic particles 64 are immobilized using a magnet adjacent to the transparent window and the fluorophores 62 have been excited, the emitted signal from the fluorophores 62 is relatively low or absent, and the amount of target component 61 can be determined.

The emitter-reader assembly shown in FIG. 9 is comprises a casing 90 comprising a plurality of not shown diodes with respective center wavelengths for exciting the respective wavelengths of the fluorophores. The emitter-reader assembly further comprises an emitter fiber bundle 91 comprising a plurality of optical fibers in light connection with the respective diodes for guiding the light towards not shown fluorophores bound to temporally immobilized magnetic particles in a micro fluidic device. The emitter fiber bundle 91 has a length section 92 adjacent to emitter output ends 93 of the optical fibers from where the light 99 is emitted.

In the length section 92 the emitter bundle 91 is merged with a reader fiber bundle 96 such that the length section is a common emitter-reader length section 92. The common emitter-reader length section 92 is held together by a sleeve 94. The reader fiber bundle 96 comprises a plurality of optical fibers having reader input ends 95 arranged to receive the light signal 99 from the fluorophores. The reader fiber bundle 96 is fixed to a connector 97 where it is connected to a not shown reading unit—e.g. a spectroscope, via a waveguide 98 e.g. in form of another fiber bundle.

The emitter output ends 93 and the reader input ends 95 are advantageously arranged in a predetermined pattern. The predetermined pattern is advantageously selected such as to obtain high exciting rate and high reading rate. The emitter output ends 93 and the reader input ends 95 are advantageously positioned immediately adjacent to the transparent window, e.g. where the magnet was arranged when immobilizing the magnetic particles and/or immediately adjacent to the magnet.

EXAMPLES

Example 1

Screening Tests

Milk samples are screened for the target analyte Ampecillin.

A system as shown in FIG. 5 is used. The micro fluidic device is in the form of a cartridge similar to the micro fluidic device of FIG. 4, but with the difference that the 5 flow channels each have their respective inlet with an inlet-well. The magnet applied is a permanent magnet arranged to immobilize magnetic particles in the reading zone.

The channels are in fluid connection to sink sections 4 and have together with the sink section 5 zones, an inlet zone 0, a zone with temporally immobilized magnetic particles 1, a zone with temporally immobilized fluorophores 2, a reading zone with a transparent window 3 and a zone with flexible wall and sink sections 4.

By having 5 separate flow channels with separate inlets it is possible to screen 5 different samples simultaneously.

The temporally immobilized magnetic particles are 1.5 μm Biomag Protein G magnetic particles from Qiagen with Ampicillin antibody loaded onto Protein G. 1 μL of 0.4% by weight of the magnetic particles solution in buffer is deposited in the channel (zone 1) and dried down.

The temporally immobilized fluorophores are Qdot 655 Biotin Conjugate from Invitrogen loaded with Ampicillin. 1 μL of 15 nM buffer solution of the Qdot 655 is deposited in the channel (zone 2) and dried down.

As an internal reference signal Bio-Adembeads Streptavidin magnetic beads from Ademtech are labeled with Qdot 605 biotin conjugate from Invitrogen.

The Bio-Adembeads Streptavidin magnetic beads are deposited in the fluorophores zone (zone 2).

The tests are performed as follows:

5 different milk samples are loaded in the 5 inlet-wells on the cartridge. Each sample is drawn into the respective channel of the cartridge and re-suspends the magnetic particle in zone 1. Incubation is done by cycling the flow for 20 seconds over the site comprising the immobilized magnetic particles to re-suspend these and allow the magnetic particles to catch target analytes in the exposed sample volume. The sample is then drawn further into the channels of the cartridge to zone 2 and re-suspends the Qdots. Again incubation is done by cycling the flow for 20 seconds. Finally the sample is drawn into the sink section 4 whereby the magnetic particles approaching the magnet while the sample is passing are immobilized in the reading zone.

The magnetic particles are subjected to exciting wavelength(s) and the emitted signal is recorded.

The signals recorded at 655 nm can be normalized with the signal recorded at 605 nm. The resulting signal will show whether the respective sample comprises the target analyte.

Example 2

Quantitative Determination of One Target Analyte

Mouse serum is tested for Mouse IgG. The samples are prepared by dilution of the Mouse serum in buffer.

A system as shown in FIG. 5 is used. The micro fluidic device is in the form of a cartridge similar to the micro fluidic device of FIG. 4 but with the difference that the micro fluidic device comprises 2 flow channels with a common inlet with an inlet-well and the micro fluidic device comprises a common sink section in fluid connection with the flow channels. The micro fluidic device further comprises a flexible wall section which is common for the flow channels. In this example it is important that the flow channels and the deposition in the flow channels are essentially identical.

The magnet applied is a permanent magnet arranged to immobilize magnetic particles in the reading zone.

The channels in flow connection with the sink sections 4 have 5 zones, a common inlet zone 0, a zone with temporally immobilized fluorophores 1, a zone with temporally immobilized magnetic particles 2, a reading zone with a transparent window 3 and a common zone with flexible wall and sink section 4. It should be observed that the magnetic particles zone and the fluorophores zone in this example are reversed compared to the order thereof in example 1.

By having 5 separate flow channels with separate inlet it is possible to screen 5 different samples simultaneously.

The temporally immobilized magnetic particles are 1.5 µm Biomag Protein G magnetic particles from Qiagen with mouse IgG loaded onto Protein G. 1 µL of 0.4% by weight of the magnetic particles solution in buffer is deposited in the channel (zone 2) and dried down.

The temporally immobilized fluorophores are Qdot 655 Goat F(ab')2 anti-Mouse IgG Conjugate (H+L) from Invitrogen. 1 µL of 15 nM buffer solution of the Qdot 655 is deposited in the channel (zone 1) and dried down.

Additionally a surfactant in the form of a detergent is applied in the sink section.

The tests are performed as follows:

Sample is applied in the well and drawn into the channels of the cartridge and re-suspends Qdots in zone 1. Incubation is done by cycling the flow for 20 seconds over the site for the immobilized Qdots to re-suspend these. The sample is then drawn further into the channels of the cartridge and re-suspends the immobilized magnetic particles in zone 2 and simultaneously the magnetic particles will catch analytes and Qdots. The analytes and Qdots will compete about the capture sites of the magnetic particles. Again incubation is done by cycling the flow for 20 seconds. Finally the sample is drawn into the sink section whereby the magnetic particles approaching the magnet while the sample is passing are immobilized in the reading zone. In the sink section the dried down detergent is dissolved and thereby the surface tension of the sample is lowered. To reduce background noise, the sample is finally pushed back into the channels where it is flushing the reading zone of non-immobilized sample but leaving the magnetic particles with the signal at the reading site. The detergent improves the flushing of the fluidic system.

The magnetic particles are subjected to exciting wavelength(s) and the emitted signal is recorded.

By comparing the obtained signals by a reference schedule as described above, e.g. a calibration curve, the quantitative determination can be obtained.

Example 3

Quantitative Determination of Two Target Analytes

Milk sample tested for the target analyte Ampecillin and the target analyte Tetracyclin.

A system as shown in FIG. 5 is used. The micro fluidic device is in the form of a cartridge similar to the micro fluidic device of FIG. 4 but with the difference that the micro fluidic device comprises 2 flow channels with a common inlet with an inlet-well, a common flexible wall section and in fluid connection with a common sink section. In this example it is desired that the flow channels and the deposition in the flow channels are essentially identical for improved precision.

The magnet applied is a permanent magnet arranged to immobilize magnetic particles in the reading zone.

The channels in fluid connection with the sink section 4 have 5 zones, a common inlet zone 0, a zone with temporally immobilized magnetic particles 1, a zone with temporally immobilized fluorophores 2, a reading zone with a transparent window 3 and a common zone with flexible wall and sink 4.

The temporally immobilized magnetic particles are 1.5 µm Biomag Protein G magnetic particles from Qiagen with Ampicillin antibody loaded onto Protein G and 1.5 µm Biomag Protein G magnetic particles from Qiagen with Tetracyclin antibody loaded onto Protein G. 1 µL of 0.2% by weight of each of the magnetic particles solution in buffer is deposited in the channel (zone 1) and dried down.

The temporally immobilized fluorophores are Qdot 655 Biotin Conjugate from Invitrogen loaded with Ampicillin and Qdot 605 Biotin Conjugate from Invitrogen loaded with Tetracyclin. 1 µL 7.5 nM buffer solutions of both Qdots are deposited in the channel (zone 2) and dried down.

The tests are performed as follows:

Sample is applied in the well and drawn into channels of the cartridge and re-suspends magnetic beads in zone 1. Incubation is done by cycling the flow for 20 seconds over the site for the immobilized magnetic particles to re-suspend these and allow the magnetic particles to catch target analytes in the exposed sample volume. The sample is then drawn further into the channels of the cartridge and re-suspends the Qdots in zone 2. Again incubation is done by cycling the flow for 20 seconds. Finally the sample is drawn into the sink section whereby the magnetic particles approaching the magnet while the sample is passing are immobilized in the reading zone. The magnetic particles are subjected to exciting wavelength(s) and the emitted signal is recorded.

The recorded signal at 655 nm is related to the content of Ampicillin in the sample. The recorded signal at 605 nm is related to the content of Tetracyclin in the sample.

Example 4

Quantitative Determination of One Target Analyte in Whole Blood

Whole blood is tested for CRP. The sample is undiluted. A system as shown in FIG. 5 is used. The micro fluidic device is in the form of a cartridge similar to the micro fluidic device of FIG. 4 but with the difference that the micro fluidic device comprises 2 flow channels with a common inlet with an inlet-well and with a common flexible wall section and in fluid communication with a common sink section. In this example it is important that the flow channels and the deposition in the flow channels are essentially identical.

The magnet applied is a permanent magnet arranged to immobilize magnetic particles in the reading zone.

The channels in fluid connection with a sink section 4 have 5 zones, a common inlet zone 0, a zone with temporally immobilized fluorophores 1, a zone with temporally immobilized magnetic particles 2, a reading zone with a transparent window 3 and a common zone with flexible wall and sink section 4. By having 5 separate flow channels with separate inlets it is possible to screen 5 different samples simultaneously.

The temporally immobilized magnetic particles are 1.5 μm Biomag Protein G magnetic particles from Qiagen with CPR loaded onto Protein G. 1 μL of 0.4% by weight of the magnetic particles solution in buffer is deposited in the channel (zone 2) and dried down.

The temporally immobilized fluorophores are Qdot 655 Biotin Conjugate from Invitrogen loaded with CRP antibody. 1 μL of 15 nM buffer solution of the Qdot 655 is deposited in the channel (zone 1) and dried down.

The tests are performed as follows:

Sample is applied in the well and is drawn into cartridge and re-suspends Qdots in zone 1. Incubation is done by cycling the flow for 40 seconds over the site for the immobilized Qdots. The sample is then drawn further into channels of the cartridge and re-suspends the immobilized magnetic beads and simultaneously the magnetic particles will catch analytes and Qdots. The analytes and Qdots will compete about the capture sites of the magnetic particles. Again incubation is done by cycling the flow for 40 seconds. Finally, the sample is drawn into the sink section whereby the magnetic particles approaching the magnet while the sample is passing are immobilized in the reading zone.

The magnetic particles are subjected to exciting wavelength(s) and the emitted signal is recorded.

By comparing the obtained signals by a reference schedule as described above, e.g. a calibration curve, the quantitative determination can be obtained.

Example 5

Example 1 is repeated using an extract of crushed beef diluted with water. Samples with different degree of dilution are applied.

Example 6

Example 2 is repeated with the difference that the sample is mixed with the magnetic particles and the fluorophores before applying the sample to the well and drawing it into the channels of the cartridge.

The mouse serum is diluted in a buffer and mixed with magnetic particle solution and q-dot solution in a vial and is incubated for 5 minutes prior to application in the well and introduction into the channels.

The sample can immediately be drawn into the sink section whereby the magnetic particles approaching the magnet while the sample is passing are immobilized in the reading zone.

Example 7

Example 2 is repeated with the difference that the system is flushed with the sample by pushing the sample from the sink section into the channels to flush the reading zone from non-immobilized sample but leaving the magnetic particles with the signal at the reading site.

When the system has been flushed, a read-out module is positioned above one channel. The Qdots are excited using a 420 LED and the emitted spectrum is recorded. An algorithm running on a PC finds and records the peak light intensity at 655 nm and 605 nm. The read-out module is then positioned above the next channel.

Some preferred embodiments have been shown in the foregoing, but it should be stressed that the invention is not limited to these, but may be embodied in other ways within the subject-matter defined in the following claims.

The invention claimed is:

1. A method for quantitative or qualitative determination of at least one target component in a liquid sample, the method comprises:
    providing a plurality of magnetic particles comprising one or more capture sites for the target component on the respective surfaces of the magnetic particles;
    providing a plurality of fluorophores coupled to a component which is identical or homolog to the at least one target component so that the component is also able to bind to said capture sites of the magnetic particles;
    arranging the fluorophores and said magnetic particles at a distance from each other inside a flow channel of a micro fluidic device comprising a transparent window to the flow channel, and temporarily immobilizing the fluorophores and said magnetic particles in the flow channel of the micro fluidic device, such that they cannot bind to each other prior to feeding the liquid sample to the flow channel, the flow channel is defined by a groove or walls;
    feeding said liquid sample suspected of containing the at least one target component into said flow channel to resuspend the fluorophores and the magnetic particles, wherein the feeding of said liquid sample into said flow channel comprises using an actuator for moving a flexible wall section of the flow channel or of a sink section in fluid connection with the flow channel;
    mixing said liquid sample suspected of containing the at least one target component, said fluorophores, and said magnetic particles simultaneously inside said flow channel while allowing said at least one target component, if present, to compete with the fluorophores with the capture sites of the magnetic particles; and
    at least temporally immobilizing said magnetic particles adjacent to said transparent window using a magnet, exciting the fluorophores bound to the immobilized magnetic particles with an electromagnetic beam, reading signals emitted from fluorophores captured by said immobilized magnetic particles and performing a quantitative or qualitative determination of said at least one target component based on the read signals.

2. The method of claim 1, wherein the liquid sample comprises a biological fluid or a fraction of a biological fluid.

3. The method of claim 1, wherein the liquid sample comprises human, animal, or vegetable fluids selected from at least one of blood, saliva, urine, milk, cytosol, intracellular fluid, interstitial fluid, tissue fluid, and one or more fractions or mixtures thereof, or suspended biological solids.

4. The method of claim 1, wherein the at least one target component comprises a microorganism selected from bacterial pathogens, viral pathogens, or fungal pathogens.

5. The method of claim 1, wherein the at least one target component comprises at least one of one or more of the groups cells, proteins, nucleotides, carbohydrates, or lipids.

6. The method of claim 1, wherein the magnetic particles are coated magnetic particles comprising a coating comprising the captures sites for the at least one target component.

7. The method of claim 1, wherein the fluorophores are comprised of at least one of quantum dots, aromatic probes or conjugated probes.

8. The method of claim 1, wherein the fluorophores are quantum dots that emit one or more discrete frequencies of light when stimulated by a light source and wherein each quantum dot comprises a core of an excitable material and an organic coating which is coupled to the component which can bind to the capture sites of the magnetic particles.

9. The method of claim 1, wherein the actuator is a step motor driven actuator.

10. The method of claim 1, wherein said at least temporally immobilized magnetic particles are subjected to said electromagnetic beam such that at least a part of possible fluorophores captured by said capture sites of the magnetic particles are excited, and subsequently the emitted signal from any captured fluorophores is read and a quantitative or qualitative determination of said at least one target component based on the read signal is performed.

11. The method of claim 1, wherein said at least temporally immobilized magnetic particles are released from magnetic forces applied by the magnet prior to being subjected to said electromagnetic beam.

12. The method of claim 1, wherein the quantitative or qualitative determination of at least one target component in the liquid sample is performed by comparing the read signal(s) with signals obtained from liquid samples of known composition.

13. The method of claim 1, wherein the quantitative or qualitative determination of the at least one target component in the liquid sample is performed by multiplexing the read signals from different groups of fluorophores using reference fluorophores with a different exciting wavelength.

14. The method of claim 1, wherein the plurality of fluorophores are configured to bind directly to said capture sites of the magnetic particles.

15. The method of claim 1, wherein the micro fluidic device comprises a substrate with a groove for the flow channel and a foil covering the flow channel.

16. The method of claim 1, wherein the micro fluidic device comprises an inlet for the liquid sample.

17. The method of claim 1, wherein the arranging and immobilizing of the fluorophores and the magnetic particles at a distance from each other inside the flow channel comprises temporally immobilizing of the fluorophores and the magnetic particles in respectively a first zone and a second zone separate from the first zone, wherein the first zone and the second zone are arranged between an inlet zone and a reading zone where said magnetic particles are at least temporally immobilized adjacent to the transparent window.

18. The method of claim 1, wherein the liquid sample is brought into the flow channel by moving a flexible wall section of the flow channel or a sink section in fluid communication with the flow channel to press out air of the flow channel and there after sucking the liquid sample into the flow channel to resuspend and mixing with the temporally immobilized fluorophores and magnetic particles.

19. The method of claim 1, wherein said method comprises performing two or more parallel assays on the liquid sample for quantitative or qualitative determination of the at least one target component, each assay comprises:
  bringing a part of the liquid sample into contact with said fluorophores and said magnetic particles in the flow channel of the micro fluidic device comprising the transparent window; and
  at least temporally immobilizing said magnetic particles adjacent to said transparent window using the magnet, emitting exciting electromagnetic beam towards said immobilized magnetic particles, and reading signals emitted from fluorophores captured by said immobilized magnetic particles,
  wherein the respective parallel assays are performed in respective flow channels using respective magnetic particles and respective fluorophores.

20. The method of claim 19, wherein the fluorophores and/or the magnetic particles used in one of the two or more parallel assays differ from the fluorophores and/or the magnetic particles used in another one of the two or more parallel assays.

* * * * *

UNITED STATES PATENT AND TRADEMARK OFFICE
CERTIFICATE OF CORRECTION

PATENT NO. : 10,859,571 B2  
APPLICATION NO. : 14/409703  
DATED : December 8, 2020  
INVENTOR(S) : Martin Bak Heller, Bent Overby Glostrup and Niels Kristian Bau-Madsen Page 1 of 1

It is certified that error appears in the above-identified patent and that said Letters Patent is hereby corrected as shown below:

On the Title Page

At (72) Inventors: Please change "Martin Bak Heller" to --Martin Heller--.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*